(12) United States Patent
Thomas et al.

(10) Patent No.: US 7,476,787 B2
(45) Date of Patent: Jan. 13, 2009

(54) ADDRESSABLE FIELD ENHANCEMENT MICROSCOPY

(75) Inventors: James L. Thomas, Cedar Crest, NM (US); Wolfgang G. Rudolph, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 415 days.

(21) Appl. No.: 11/361,018

(22) Filed: Feb. 23, 2006

(65) Prior Publication Data
US 2006/0192115 A1 Aug. 31, 2006

Related U.S. Application Data

(60) Provisional application No. 60/655,640, filed on Feb. 23, 2005, provisional application No. 60/711,448, filed on Aug. 25, 2005.

(51) Int. Cl.
G01N 23/00 (2006.01)
G01N 21/64 (2006.01)

(52) U.S. Cl. .................. 977/759; 977/700; 977/701; 977/707; 977/720; 977/834; 250/341.1; 250/368; 250/370.08

(58) Field of Classification Search .............. 250/306, 250/307, 341.1, 368, 370.08, 559.01, 559.04, 250/559.05, 559.07, 559.09, 559.13; 977/700, 977/701, 707, 720, 759, 762–764, 767, 773, 977/789, 834; 359/368, 371, 385, 386
See application file for complete search history.

(56) References Cited

U.S. PATENT DOCUMENTS

| | | | | |
|---|---|---|---|---|
| 5,479,024 A | * | 12/1995 | Hillner et al. | 250/458.1 |
| 6,465,132 B1 | * | 10/2002 | Jin | 429/231.8 |
| 7,132,677 B2 | * | 11/2006 | Kim et al. | 257/14 |
| 7,233,101 B2 | * | 6/2007 | Jin | 313/309 |
| 2005/0285128 A1 | * | 12/2005 | Scherer et al. | 257/98 |
| 2006/0192115 A1 | * | 8/2006 | Thomas et al. | 250/306 |
| 2007/0029643 A1 | * | 2/2007 | Johnson et al. | 257/651 |
| 2008/0115817 A1 | * | 5/2008 | Defries | 136/200 |

OTHER PUBLICATIONS

Jan M. Yarrison-Rice, 1990 <http://www.cas.muohio.edu/physicsweb/faculty/jayr.htm>.*

Kawata et al., "Possibility of molecular-resolution fluorescence near-field microscopy using multi-photon absorption and field enhancement near a sharp tip", J. Appl. Phys. 85(3) 1999, pp. 1294-1301.*

Bouhelier, A., et al., "Plasmon-coupled tip-enhanced near-field optical microscopy", *Journal of Microscopy*, 210(3), (Jun. 2003), 220-224.

Ghenuche, P., et al., "Cumulative plasmon field enhancement in finite metal particle chains", *Optics Letters*, 30(14), (Jul. 15, 2005), 1882-1884.

Hell, S. W., "Toward fluorescence nanoscopy", *Nature Biotechnology*, 21(11), (Nov. 2003), 1347-55.

(Continued)

*Primary Examiner*—Bernard E Souw
(74) *Attorney, Agent, or Firm*—Schwegman, Lundberg & Woessner, P.A.

(57) ABSTRACT

Systems and methods for addressable field enhancement microscopy are provided. In an embodiment, a nanoscale array of islands may be illuminated with an electromagnetic signal and addressed to differentiate signals from different islands of the nanoscale array. The differentiated signals originating from illuminating the nanoscale array may be applied to microscopy of a specimen.

48 Claims, 19 Drawing Sheets

OTHER PUBLICATIONS

Huang, S.-W., et al., "Super-Resolution Bright-Field Optical Microscopy Based on Nanometer Topographic Contrast", *Microscopy Research and Technique*, 65, (2004), 180-185.

Imura, K., et al., "Research Activities II—Department of Molecular Structure—II-A Development of Near-Field Dynamic Spectroscopy and Application to Mesophase Systems", *Annual Review 2003*, http://www.ims.ac.jp/publications/ann_rev_2003/index.html,(2003), 39-41.

Leiserson, I., et al., "Superresolution in far-field imaging", *Optics Letters*, 25(4), (Feb. 15, 2000), 209-211.

Leizerson, I., et al., "Superresolution in far-field imaging", *Journal of the Optical Society of America A*, 19(3), (Mar. 2002), 436-443.

Sandoghdar, V., et al., "Results and Thoughts on Optical Microscopy Using a Single-molecule Probe", *Single Molecules*, 2(4), (2001), 277-281.

Watanabe, T., et al., "Two-point-separation in super-resolution fluorescence microscopy based on up-conversion fluorescence depletion technique", *Optics Express*, 11(24), (Dec. 1, 2003), 3271-3276.

* cited by examiner

ADDRESSABLE FIELD ENHANCEMENT MICROSCOPY

RELATED APPLICATION

This application claims priority under 35 U.S.C. 119(e) from U.S. Provisional Application Ser. No. 60/655,640 filed 23 Feb. 2005 and from U.S. Provisional Application Ser. No. 60/711,448 filed 25 Aug. 2005, which applications are incorporated herein by reference.

FIELD OF THE INVENTION

This invention relates generally to microscopy.

DETAILED DESCRIPTION

Figure 1:
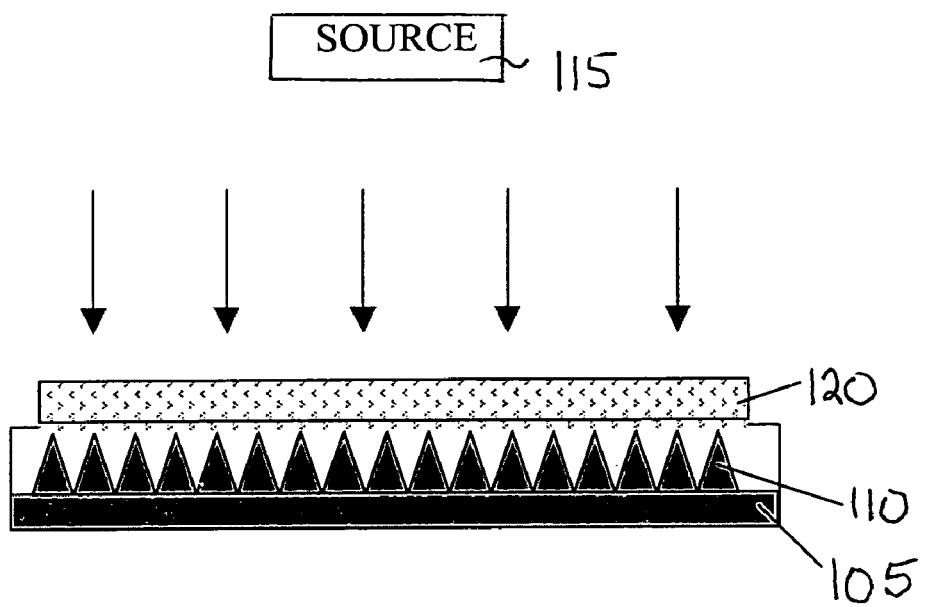
FIG. 1 shows an embodiment of a method using nanostructures on a substrate to examine a specimen, in which the illuminated nanostructured substrate provides enhanced fields or fluorescence emission to illuminate the specimen.

In the following detailed description, reference is made to the accompanying drawings which form a part hereof, and in which is shown by way of illustration specific embodiments in which the present invention may be practiced. These embodiments are described in sufficient detail to enable those skilled in the art to practice the present invention. Other embodiments may be utilized and structural, logical, and electrical changes may be made without departing from the spirit and scope of the invention. The various embodiments are not necessarily mutually exclusive, as some embodiments can be combined with one or more other embodiments to form new embodiments. The following detailed description is, therefore, not to be taken in a limiting sense.

It is well known that electromagnetic fields are strengthened near very small particles, or sharp tips of particles, composed of metals or semiconductors. Thus, it is now common practice to use nanoparticles to increase the strength of optical signals originating from nearby molecules. Illumination applied to the nanoparticle causes a very strong, local, oscillating electromagnetic field near the particle, which can excite optical processes in nearby molecules. It is possible to make nanoscale arrays of metallic or semiconductor islands, which serve the same purpose. An embodiment in accordance with the teaching of the invention provides a method for making microscopic images.

In an embodiment, a method includes illuminating a nanoscale array of islands with an electromagnetic signal and addressing the nanoscale array to differentiate signals from different islands of the nanoscale array. The differentiated signals originating from illuminating the nanoscale array may be applied to microscopy of a specimen. Various embodiments may be applied to distinguish signals originating from different islands or from different positions on a single island. If the island separation is well below the optical resolution limit, it is not generally possible to illuminate a single island. The optical resolution limit, defined by "Rayleigh's criterion," is $0.61*\lambda/NA$, where $\lambda$ is the wavelength of light used and NA is the numerical aperture of the objective lens used. An embodiment that allows distinguishing signals from different islands may thereby permit superresolution microscopy. A nanoscale array, and other apparatus described herein with "nano" as a prefix, has a dimension measured in nanometers (less than one micron).

Embodiments include various methods or combinations of these methods to distinguish signals. In an embodiment, an electrooptic method is applied. The effectiveness of the local field enhancement effect depends on the wavelength of light, the optical properties of the nanoparticle or island, and the optical properties of the surrounding medium. Electrooptic materials change their index of refraction in the presence of an electric field. By placing electrooptic material between islands, the field enhancement for any particular island can be manipulated by applying local electric fields. The local fields may be applied by applying a potential difference between nearby islands or by a separate wiring grid or pattern.

To obtain superresolution, it is not necessary to "turn off" field enhancement at all islands except one. If the field enhancement effect at a single island can be modulated, then a subtractive or lock-in detection method can isolate the signal originating at the specified island. Also, interlaced grids of islands whose elements separation can be resolved by far-field microscopy can be addressed one at a time.

In an embodiment, a thermal method is applied. Vanadium oxide is an unusual material that undergoes a semiconductor-to-metal transition at about 67° C. Nanoparticles of $VO_2$ may be synthesized and assembled into arrays. Above the transition temperature, $VO_2$ has a strong electron resonance ('plasmon'), which will give rise to strong local field enhancement. If a laser beam is situated over an array of $VO_2$ nanoparticles, the particle at the center of the beam will be warmed much more quickly than particles not centered. Not only is the intensity higher, but heat conduction will cool the off-center particles, by heat transfer to non-illuminated regions. The semiconductor-to-metal transition in only the center particle may be activated by controlling the deposition of energy from the exciting beam. When the center particle becomes metallic, plasmons will be more strongly excited and these will give near-field enhancement in the vicinity of the center particle. The excitation can be through a multi-photon absorption to better confine the transition to the beam center, thereby increasing the resolution. Vanadium oxides of other stoichiometries may be used, other materials with semiconductor-metal transitions may be used, or combinations of materials with semiconductor-metal transitions may be used.

In an embodiment, a polarization method is applied. Field enhancement may depend on the polarization of the incident beam. When the electric field is directed toward or away from a sharp tip or corner, strong field enhancement results. When the field is orthogonal to the tip or corner, there is little enhancement. In an embodiment, two orthogonal polarizations of exciting light are used to cause field enhancement at, for example, two sets of opposite corners of a square metallic island. If the opposite corners are separated by the optical resolution limit, the method increases the linear resolution by a factor of $\sqrt{2}$. Other possibilities include interlaced grids with elements whose shape favor certain excitation beam profiles, for example Gaussian vs Laguerre beams to accomplish the optical addressing.

In an embodiment, array-based field enhancement/quantum dot nanoscopy may be applied to various specimens. Light microscopy has proven to be a remarkably powerful tool in the biomedical sciences, in spite of its resolution, diffraction-limited to the order of the optical wavelength. The principal strength of light microscopes lies in the ability to image dynamic, often living, biological specimens and tissues. Recent work in multiphoton excitation for fluorescence and in harmonic microscopy has dramatically extended the capabilities of this instrument. The development of near-field optical microscopy has broken the "resolution barrier" and has allowed researchers to optically image sub-wavelength structures.

In various embodiments, nanoarray structures may be applied to light microscopy, where these structures and techniques may be applied to studies of cell and synthetic bilayer membranes. Nanolithographic techniques will continue to improve in the coming few years, and that very soon features in the ten-nanometer size range will be readily and inexpensively achievable. The production of large-area (cm scale) line arrays with a half-pitch of 45 nm without using e-beam lithography has been demonstrated. In various embodiments, the nanoarrays may be light emitters (as in quantum dot nanoarrays) or electric-field amplifiers (as in field enhancement arrays.) Extending the resolution enhancement known from single-tip, near-field optical microscopes to the massively parallel structures may provide the resolution to maintain the advantages of far-field imaging, such as speed, field of view, and versatility. With progress in addressing individual array elements whose spacing and size is well below 50-nm, video-rate imaging with near-field resolution in imaging modes most relevant to the life sciences may be provided.

With today's technology, arrays can be made at or somewhat below the resolution limit obtained from visible (VIS) illumination. When used as a scanning probe, a small array of sources can multiplex the signal, allowing for much more rapid image collection. This is particularly important for the life sciences where video-rate imaging allows for the observation of many dynamic biological processes. In local field-enhancement, excitation can be restricted to certain parts of the elements (for example, opposite corners in a small metallic square, using polarization effects). Because of this restriction, the resolution can be effectively increased to well below the far-field resolution limit. For techniques such as harmonic generation and multiphoton fluorescence, short-pulse lasers and very high instantaneous powers are typically required. Arrays of field enhancement elements can give strong local fields with moderate incident fields, and the spatial field distribution can be tailored. Various embodiments provide for structures and methods to construct nanoarrays, to characterize their physical/optical properties, to employ them in biophysical studies, and to work toward a next generation of addressable arrays.

Two approaches may provide parallel efforts: quantum dot arrays and field enhancement arrays. FIG. 1 shows an embodiment of an approach using nanostructures 110 on a substrate 105 to examine a specimen 120. Far field excitation from a source 115, generally a focused laser, will excite nanostructures 110. Nanostructures 110 then serve as local sources for near-field imaging. Enhanced electromagnetic fields or fluorescence emission from nanostructures 110 illuminates specimen 120, which may be a biological specimen. Specimen 120 may respond via a number of alternative mechanisms: one- or multi-photon fluorescence, either radiatively or non-radiatively excited; harmonic generation, or possibly through polarization-dependent scattering/reflectivity. While the optical addressing of the array elements limits the resolution attainable, methods to address individual array elements may provide for resolution enhancements. Configuration of a specimen is not limited to being disposed on the nanostructure that provides enhanced fields for microscopy of the specimen, but may have other configurations such that the specimen is in proximity to the nanostructure such that the nanostructure acts as a source of illumination of the specimen for microscopy of the specimen.

In various embodiments, uniform arrays of III-V semiconductor quantum dots (QD) may be applied in imaging modes. QD emission can be used for fluorescence imaging, and the polarized nature of the emission can be used for fluorescence depolarization (to study rotational motion of biomolecules, for example) and for other imaging modalities. In an embodiment, individual electrical addressing of quantum dots may be conducted. As is known to those skilled in the art, single quantum dot electroluminescence has been observed in apertured systems. In various embodiments, field enhancement arrays may be applied for multiphoton microscopies, where quantum dots (which are single-photon emitters) typically cannot serve. In embodiments, arrays may also be applied to second harmonic generation in cell and artificial membranes. The arrays may be used to study the membrane disposition of an important cell signaling protein and to measure membrane potentials in resting and stimulated cells.

Stranski and Krastanow suggested in 1938 that the growth of two materials with different lattice constants would cause the formation of small islands, rather than flat layers. These islands are termed self-assembled quantum dots. Several methods have been used by various researchers to define the QD nucleation sites in the growth plane, including scanning tunneling microscope-assisted nanolithography, electron-beam lithography, and optical lithography. The regrowth of patterned QDs has been accomplished using molecular beam epitaxy, chemical beam epitaxy, and metalorganic chemical vapor deposition.

The formation of a large, dense and uniform QD array is a complex task requiring a stable, uniform patterning process that yields a clean, undamaged surface for regrowth. In an embodiment, the position and size of Stranski-Krastanov growth mode (SK) quantum dots is controlled by first creating a square pattern of truncated GaAs pyramids, on top of which QDs are grown. The GaAs truncated pyramid serves several purposes. It forms a small plateau on which the QD forms and it separates the optically active QD from the processed interface at the pyramid base. To attain fast, large-scale exposure, an optical lithography patterning method may be employed. This patterning process has previously been used for homoepitaxial regrowth using molecular beam epitaxy. The basic structure for processing the growth mask consists of a negative photo resist (PR) film, a 45 nm-thick $SiO_2$ layer, and a GaAs (001) substrate. A 2D array of holes is formed in the PR using an interferometric lithography technique. The pattern is transferred to the $SiO_2$ film with dry etching. Using a very high quality $SiO_2$ film may prevent pinhole formation during the etching process. The patterning technique and subsequent processing to generate the $SiO_2$ pattern are fully described in the reference by Lee, Stintz, and Brueck. See, S. C. Lee, A. Stintz, and S. R. J. Brueck, "Nanoscale Limited Area Growth of InAs Islands on GaAs (001) by Molecular Beam Epitaxy," J. applied Phys. 91 (2002) 3282-3288. The resulting pattern features 100-200 nm diameter holes on a 360 nm pitch along the [110] direction.

The patterned, truncated pyramids may be grown in a vertical metal organic chemical vapor deposition reactor (MOCVD) at 60 torr and 800° C. The patterning and regrowth methodology results in highly crystalline InAs pyramids, which may be confirmed by high resolution transmission electron microscopy (HRTEM) images and high-resolution X-ray reciprocal space mapping (HRXRSM). After the truncated pyramids are grown, the temperature is lowered to 500° C. and the InAs QDs are grown. Other techniques may be used to form the desired structures.

Figure 2A:
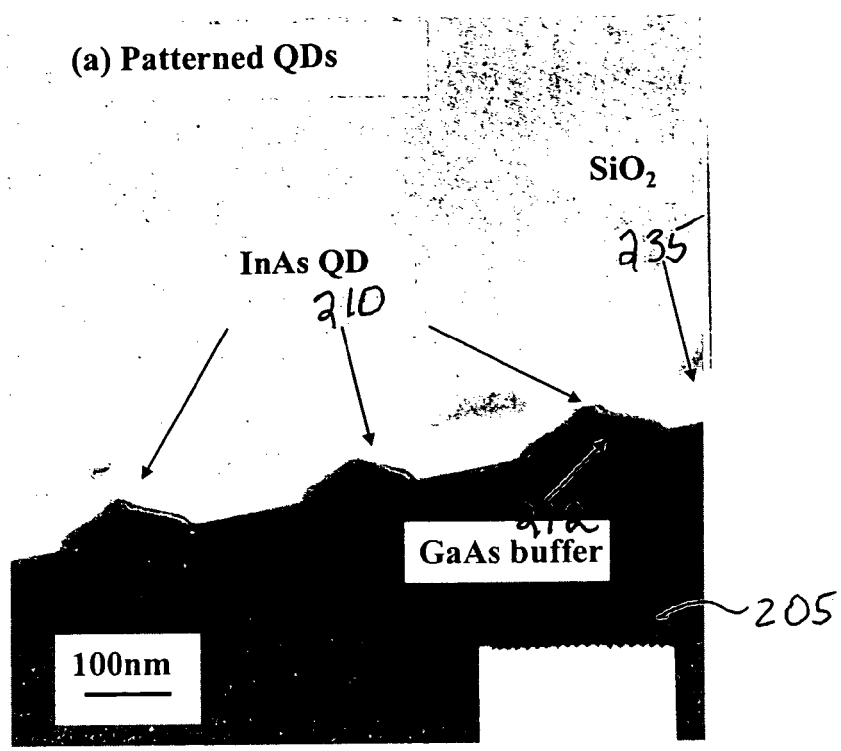
FIGS. 2A-2B show TEM images illustrating an array of patterned quantum dots and a single InAs quantum dot grown atop a truncated GaAs pyramid.
Figure 2B:
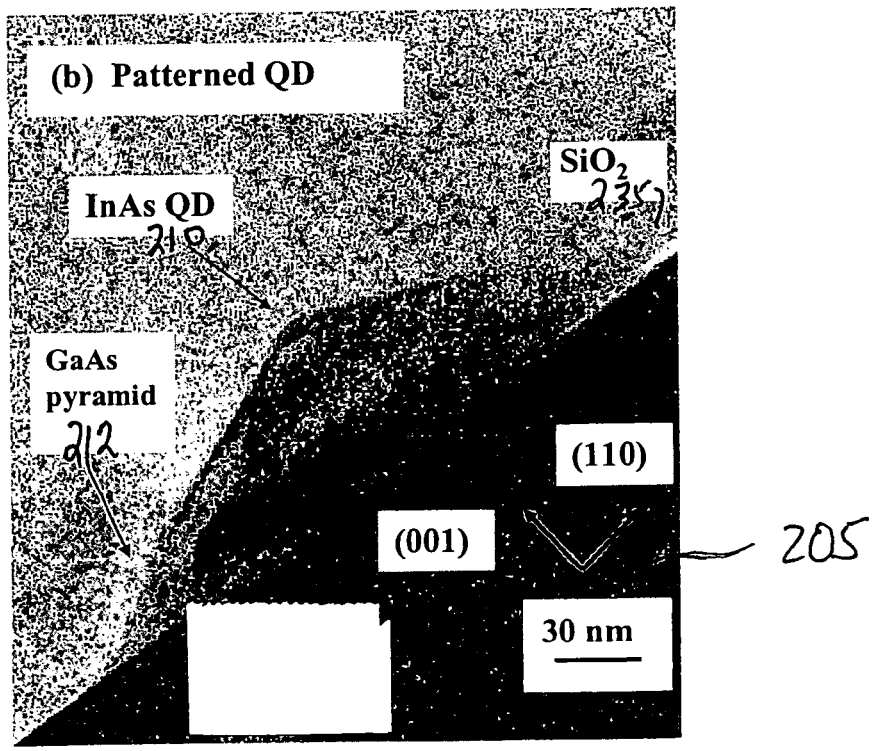
Figure 2C:
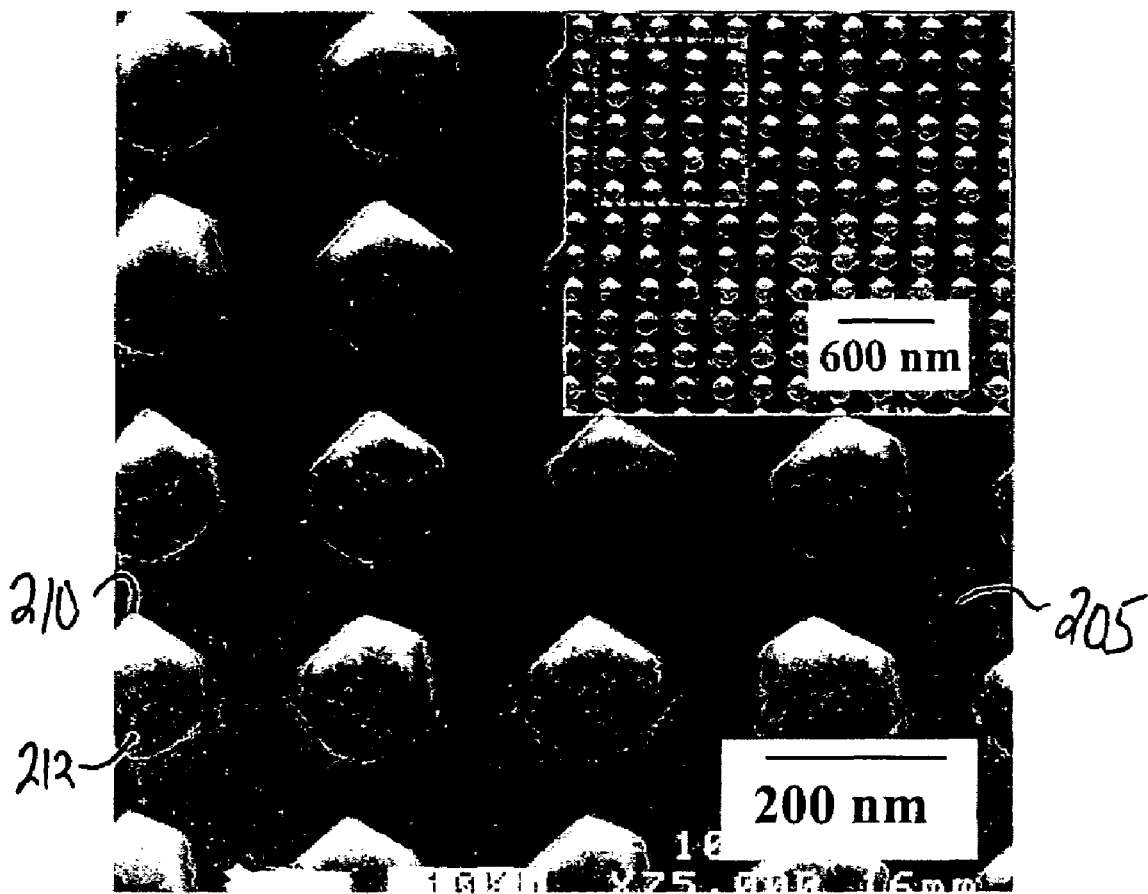
FIG. 2C shows a SEM top view of the square array of the patterned quantum dots of FIG. 2A.

FIGS. 2A-2B show TEM images illustrating an array of patterned quantum dots and a single InAs quantum dot grown atop a truncated GaAs pyramid. See, Birudavolu, S., N. Nuntawong, G. Balakrishnan, Y. C. Xin, S. Huang, S. C. Lee, S. R. J. Brueck, C. P. Hains, and D. L. Huffaker. "Selective Area Growth of InAs Quantum Dots Formed on a Patterned GaAs Substrate," Appl. Phys. Lett. 85(12): 2337-2339. 2004. FIG. 2A shows patterned InAs QDs 210 on truncated GaAs buffers 212 on a GaAs substrate 205. FIG. 2B shows a single InAs QD 210 on a truncated GaAs pyramid 212 on GaAs substrate 205. FIG. 2C shows a SEM top view of the square array of InAs QDs 210 on truncated GaAs pyramids 212 on GaAs substrate 205. Regular arrays of InAs quantum dots (QDs) 210 on a patterned GaAs substrate 205 may be formed using metal organic chemical vapor deposition. As shown in FIG. 2A, the pyramid base diameter is approximately 150 nm as determined by the $SiO_2$ mask 235. The diameter of the resulting QDs varies from about 30 nm to about 40 nm depending on variation in the mask. With specific growth conditions, highly crystalline QDs with photoluminescence spectra peak at 1.3 μm at room temperature may be formed. In an embodiment, the inhomogeneously broadened linewidth is about 50 meV, due to variations in the patterning and growth.

In the conventional strain-driven self-assembled quantum dot (SAQD) growth process, nonuniformity in the wetting layer gives rise to quantum dot nucleation. The nucleation sites are weakly linked to surface steps that are not uniformly distributed. The QD nucleation sites are thus distributed randomly on the growth surface. The random nucleation results in a non-uniform QD size distribution and a broadened inhomogeneous linewidth, typically >20 meV. Embodiments of the pyramidal procedure promote more uniform size distribution and precise localization of each QD. The pyramidal epistructure reduces non-radiative centers caused by dangling bonds and strain-related defects. Such a structure may provide an inhomogeneously broadened linewidth similar to a homogeneously broadened linewidth of 10 meV at 300° K and less than 1 meV at 4° K.

Figure 3:
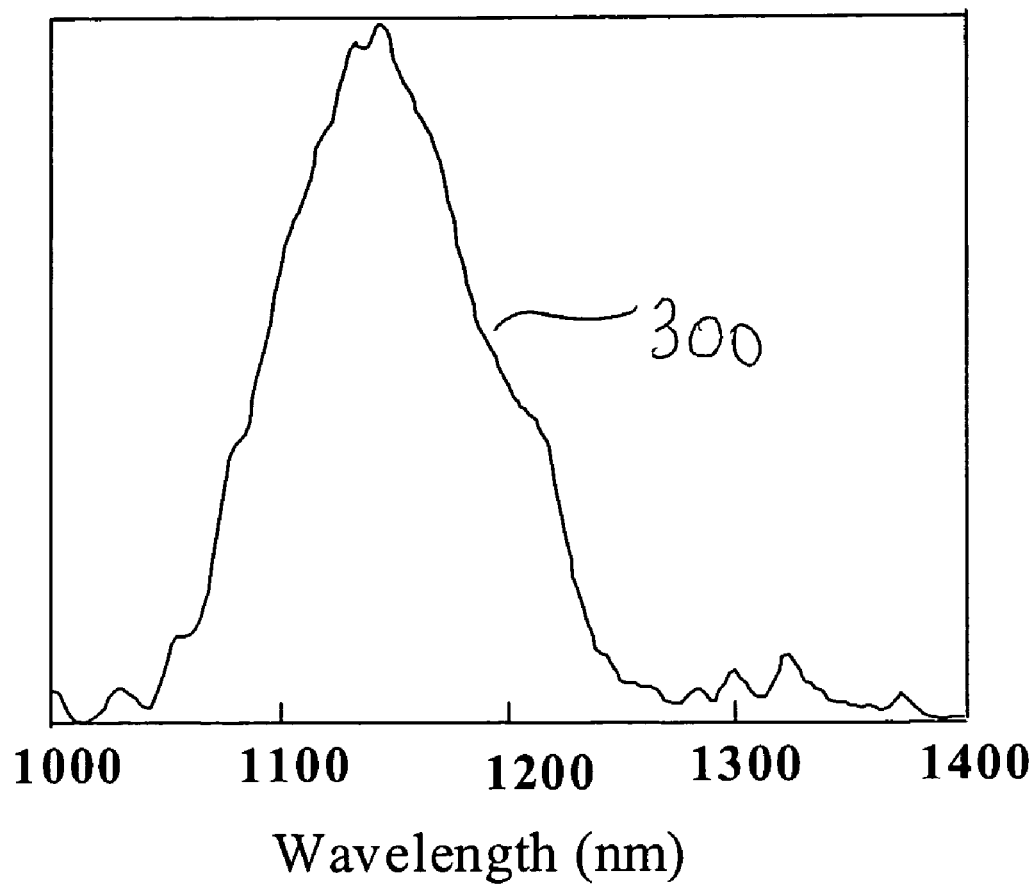
FIG. 3 demonstrates electroluminescence obtained from pyramidal quantum dot arrays.

FIG. 3 demonstrates electro-luminescence 300 from pyramidal quantum dot arrays at 120° K. This work has been conducted by colleagues in the S. R. J. Brueck research group of the Center for High Technology Materials (CHTM) at the University of New Mexico. The device resistance (12 Ω) and the leakage current (20 nA) both indicate a very clean and high quality interface with minimum dangling bond density.

In various embodiments, quantum dot array sources are used for microscopy of a variety of specimens. In other embodiments, nanostructures for field enhancement microscopy are used for microscopy of a variety of specimens. Resonant oscillations of conduction electrons in metals and semiconductors (plasmons) can give rise to strong local field enhancement, when excited with light of an appropriate frequency, polarization, and, in some cases, angle of incidence.

Figure 4A:
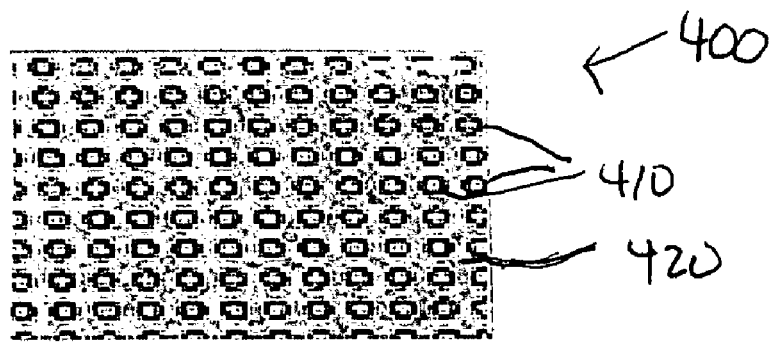
FIG. 4A shows a scanning electron micrograph of an embodiment of a coaxial array.

FIG. 4A shows a scanning electron micrograph of an embodiment of a coaxial array 400. The coaxial array is disposed in a 100-nm thick gold film atop a glass substrate. The dark annular regions 410 are open; the remainder of the surface 420 is gold. The array spacing is 1.03 μm, and the coaxial cores are 193 or 194 nm in diameter. The coaxial array shown may be fabricated using interferometric lithography, which is ideal for making large area arrays of periodic structures. The samples may be fabricated with high uniformity over 2.5×2.5 cm² areas using a self-aligned process requiring only a single lithographic step.

Figure 4B:
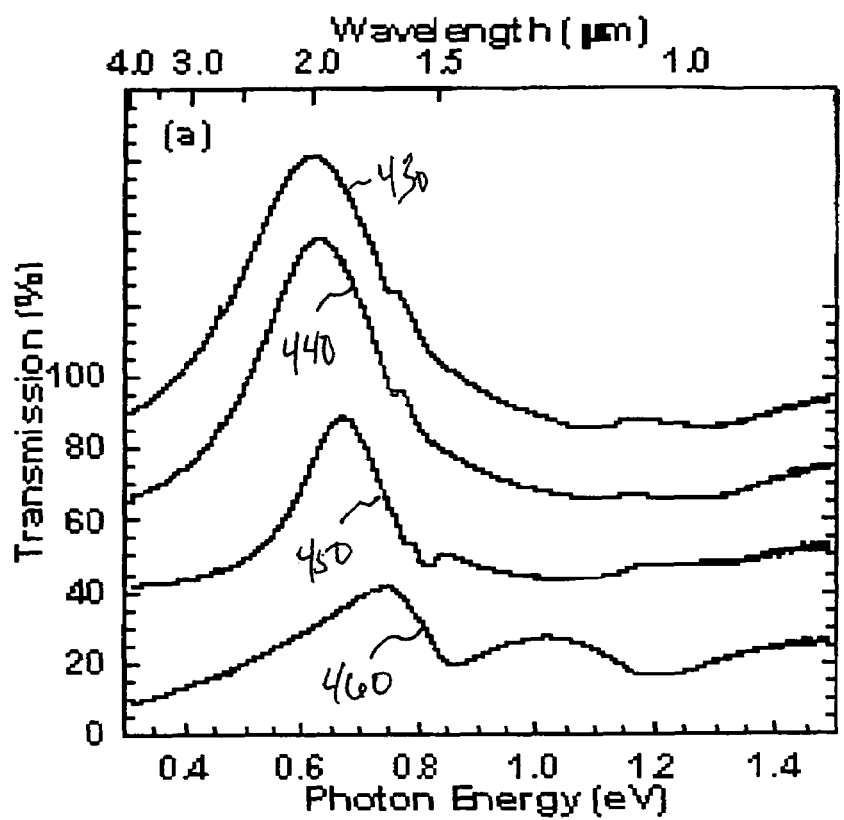
FIG. 4B shows transmissivity curves for different outer/inner diameters of the clear annuli of FIG. 4A.

FIG. 4B shows transmissivity curves for different outer/inner diameters of the clear annuli of FIG. 4A. Curve 430 is for an outer diameter of 376 nm and 194 nm core diameter coaxial hole. Curve 440 is for an outer diameter of 348 nm and 194 nm core diameter coaxial hole. Curve 450 is for an outer diameter of 298 nm and 193 nm core diameter coaxial hole. Curve 460 is for a 324 nm hole. Even though the fractional open area of the array is only 31%, and the width of the open annuli is much smaller than the wavelength, this array shows a 79% transmissivity to mid-IR light at 1.97 μm. This array effectively "concentrates" light into the annular regions, which can be used to manipulate light-matter interactions and to enhance non-linear phenomena.

Figure 4C:
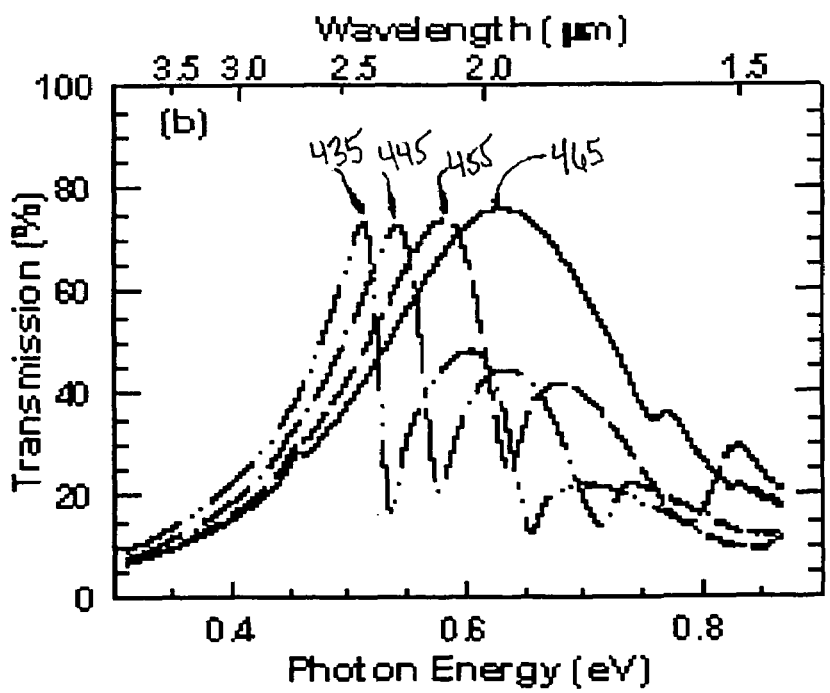
FIG. 4C shows the dependence of the transmissivity on incident angle with respect to FIGS. 4A-B.

FIG. 4C shows the dependence of the transmissivity on incident angle with respect to FIGS. 4A-B. Curve 435 is for a 60° incident angle. Curve 445 is for a 45° incident angle. Curve 455 is for a 30° incident angle. Curve 465 is for a 0° incident angle. Coaxial hole arrays show anomalously high transmissivity, owing to coupling between local plasmon resonances in the coaxial unit cell and distributed surface plasmon polaritons at the metal-dielectric interfaces. The variation with angle indicates the role of the plasmon excitations in the interaction with light. The work demonstrated in FIGS. 4A-C has been conducted by colleagues in the S. R. J. Brueck research group of the Center for High Technology Materials (CHTM) at the University of New Mexico. Coupling to distributed plasmons by a periodic array of holes is the basic physics behind the enhanced transmission in hole arrays; these annular arrays add coupling to the localized coaxial modes. In these structures these two resonances are nearly degenerate and enhance each other resulting in significantly enhanced interactions. These annular hole arrays are potentially useful "sources" for near-field non-linear microscopies.

Figure 5A:
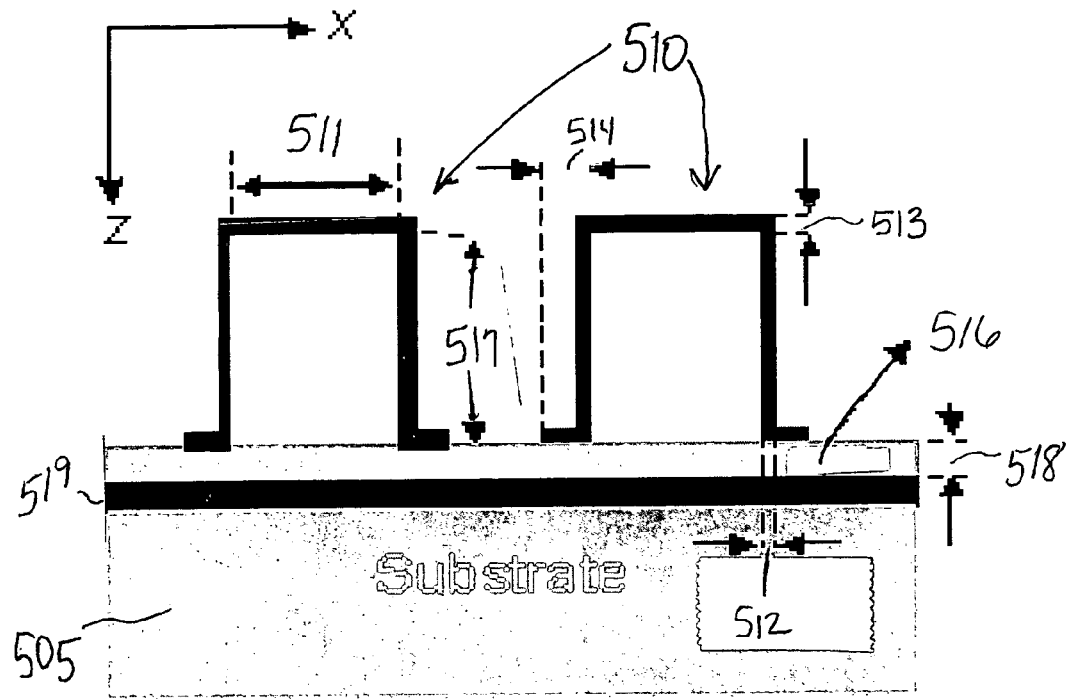
FIG. 5A illustrates a schematic of nanostructured staples.
Figure 5B:
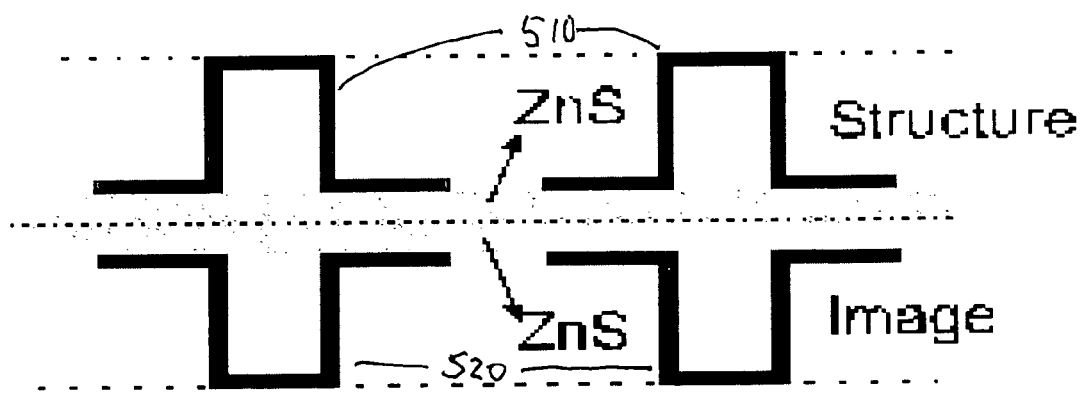
FIG. 5B illustrates the equivalent LC circuit formed between the top staple structure and its image in the metal in FIG. 5A.
Figure 5C:
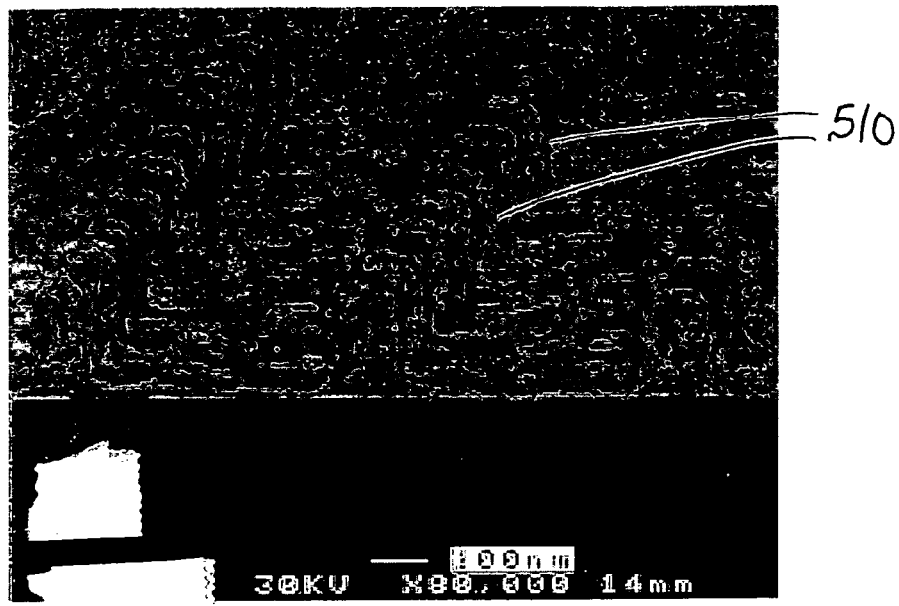
FIG. 5C shows a scanning electron micrograph showing the staple arrays of FIG. 5A.

FIG. 5A illustrates a schematic of nanostructured staples 510 on a substrate 505. Each nanostructured staples 510 may have a width 511, a thickness 512 of its vertical element, a top thickness 513, and a footing width 514 on a surface on which nanostructured staples 510 are disposed. Nanostructured staples 510 may be disposed on a ZnS layer 516. The top of each staple is a distance (height) 517 from the surface of ZnS layer 516. ZnS layer 516 has a thickness 518 and is formed on a layer 519 disposed on substrate 505. Layer 519 and staples 510 may both be composed of gold layers. Other materials may be used in the configuration of FIG. 5A. Such nanostructured staples may be employed as plasmonic structures that couple to the magnetic field of incident radiation. These "staples" act as LC inductor-capacitor tank circuits, the inductance arising from the current induced by a time-varying magnetic flux coupling through the open area. FIG. 5B illustrates the equivalent LC circuit formed between the top staple structure 510 and its image 520 in the metal in FIG. 5A. FIG. 5C shows a scanning electron micrograph showing the array of staples 510 of FIG. 5A. These structures may also be made using several steps in an interferometric lithographic approach. The work on the structures of FIGS. 5A-C may be found in Zhang, S., W. Fan, B. K. Minhas, A. Frauenglass, K. J. Malloy, and S. R. J. Brueck. "Fabrication of 1D and 2D Vertical Nanomagnetic Resonators," J. Vac. Sci. Technol. B 22(6): 3327-3330. 2004.

The size of these staple structures is appropriately 100 nm. The electrons in these structures are resonantly excited by mid-infrared light, but only when the light is properly polarized, i.e. with the electric field vector parallel to the "staple" and the magnetic field vector through the loop. Strong resonance effects give rise to as much as 50% absorption of the incident light in a single layer of staples. This strong resonance suggests that very high fields are generated in the structures, making them very useful for non-linear optics and as possible sources for non-linear microscopy. There are contributions to the inductance both from the geometric structure and from the electron inertia. This limits the scaling of these resonances to visible frequencies. Layered, multi-level plasmonic structures that combine both of these effects exhibit a true negative refractive index in the near-infrared (IR). This has been confirmed in preliminary interferometric measurements of the refractive index. Such structures may be adapted for nonlinear field-enhanced microscopy.

Figure 6:
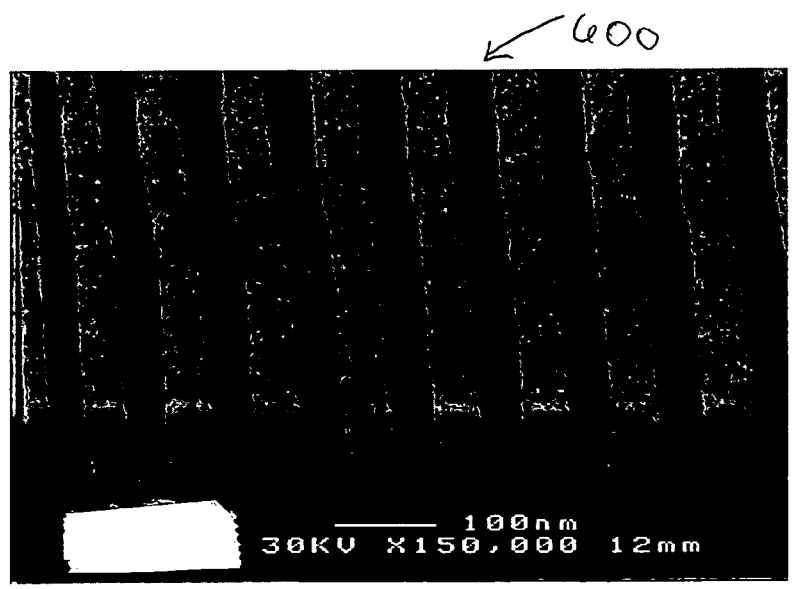
FIG. 6 shows a 1D, 45-nm line-space pattern 600 at a somewhat longer wavelength of 213 nm.

Both forming quantum dot arrays and forming arrays for field enhancement microscopy are dependent on advances in optical lithography. Interferometric lithography (IL), the interference between a small number of coherent source beams, is ideally suited to the periodic structures needed for such arrays. The limiting resolution for two-beam IL is given by $HP=\lambda/(4n \sin \theta)$, where HP is the half pitch of a dense (equal line space) pattern, $\lambda$ is the laser wavelength, n is the refractive index of the exposure medium, and $\theta$ is the angle of incidence. For example, using 193 nm photons (ArF laser) with a water immersion medium (n=1.44), the limiting pitch is 34 nm. FIG. 6 shows a previously demonstrated 1D, 45-nm line-space pattern 600 at a somewhat longer wavelength of 213 nm. See, A. K. Raub, A. Frauenglass, S. R. J. Brueck, W. Conley, R. Dammel, A. Romano, M. Sato, and W. Hinsberg, "Deep-UV Immersion Interferometric Lithography," Proc. SPIE 5377 (2004) 306-318. FIG. 6 shows a 45-nm half-pitch photoresist pattern written over a large area (>1 cm2) using immersion interferometric lithography (213 nm laser source, water immersion, q=56°). Spatial nonlinear processes allow at least a factor of two increase in the resolution to a HP of 17 nm. Thus, there is ample headroom for extending the current state of the art of optical lithography. This provides for extending the resolution of near-field and nonlinear optical microscopies.

Nonlinear microscopy with femtosecond (fs) illumination pulses has become an invaluable imaging tool in engineering, physics, and biomedical sciences. A 10-fs pulse source and a scanning microscope may be used for nonlinear imaging. Such a facility may be complemented by a fs optical parametric oscillator that allows one to tune the laser wavelength from 1.1-2.4 μm and also use the second harmonic of this radiation for multiphoton imaging.

One of the challenging problems of scanning, nonlinear (multi-photon) microscopy is obtaining short pulses at the minimum possible beam spot size, i.e. in the focal plane of a microscope objective. The key is to shape the beam and complex field in such a way that the effect of lens aberrations, especially chromatic aberrations, becomes minimal. A method to characterize the focusing of short pulses by high numerical aperture objectives based on spectral interferometry may be employed. With this information, a pre-chirper was designed providing the ability to obtain 10 fs pulses at spot sizes of 600 nm in the focal plane of high-NA objectives. These small features allow for intensities exceeding $10^{14}$ W/cm$_2$ without pulse amplification. This opens up interesting opportunities for the study of nonlinear processes and material structuring with pulses from fs oscillators without amplification.

A technique for the full-field characterization (amplitude and phase) of ultrashort pulses based on the measurement of intensity cross-correlation in an unbalanced Michelson interferometer and the pulse spectrum may be employed. For ease of use and accuracy, the retrieval procedure, Phase and Intensity from Cross-correlation and Spectrum Only (PICASO), compares favorably with the widely used FROG and SPIDER algorithms. Both techniques of characterizing short pulses may be applied to nonlinear signal and resolution enhancement using nano-structures.

Figure 7A:
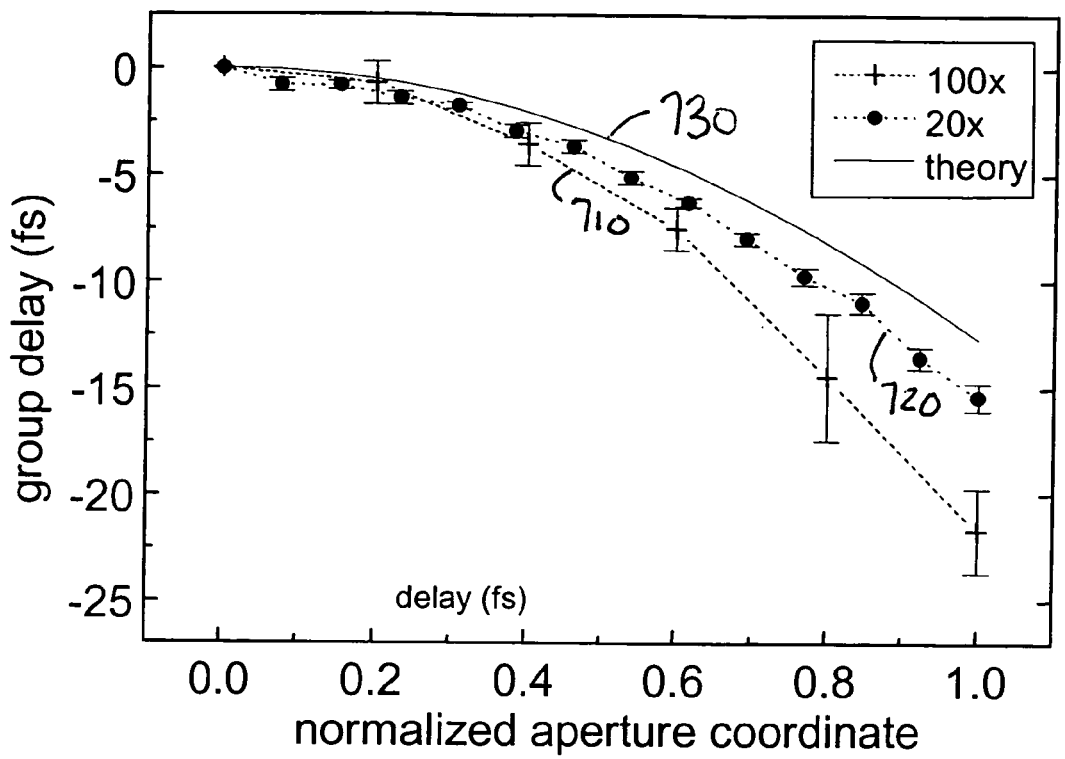
FIG. 7A shows group delay as a function of the aperture coordinate for two different microscope objectives.
Figure 7B:
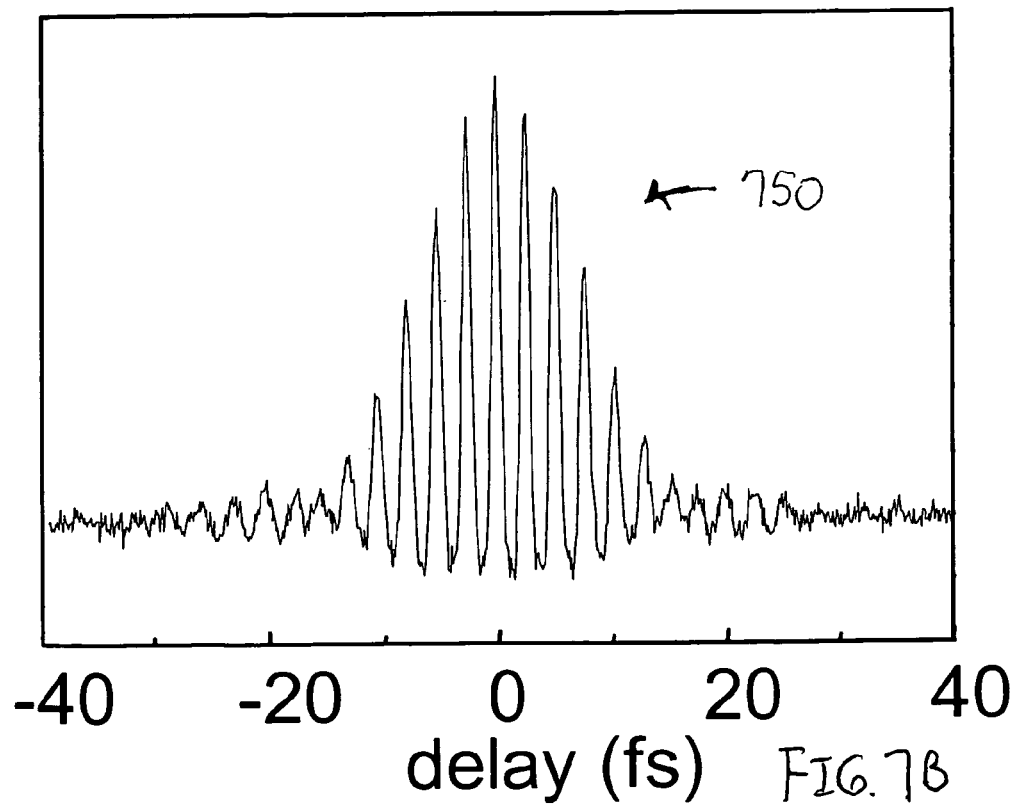
FIG. 7B shows the autocorrelation of a 9 fs pulse obtained in the focus of a 100× objective.

FIG. 7A shows group delay as a function of the aperture coordinate for two different microscope objectives. Curve 710 is for a 100× microscope objective. Curve 720 is for a 20× microscope objective. Curve 730 is a curve based on theory. FIG. 7B shows the autocorrelation 750 of a 9 fs pulse obtained in the focus of a 100× objective.

Figure 8:
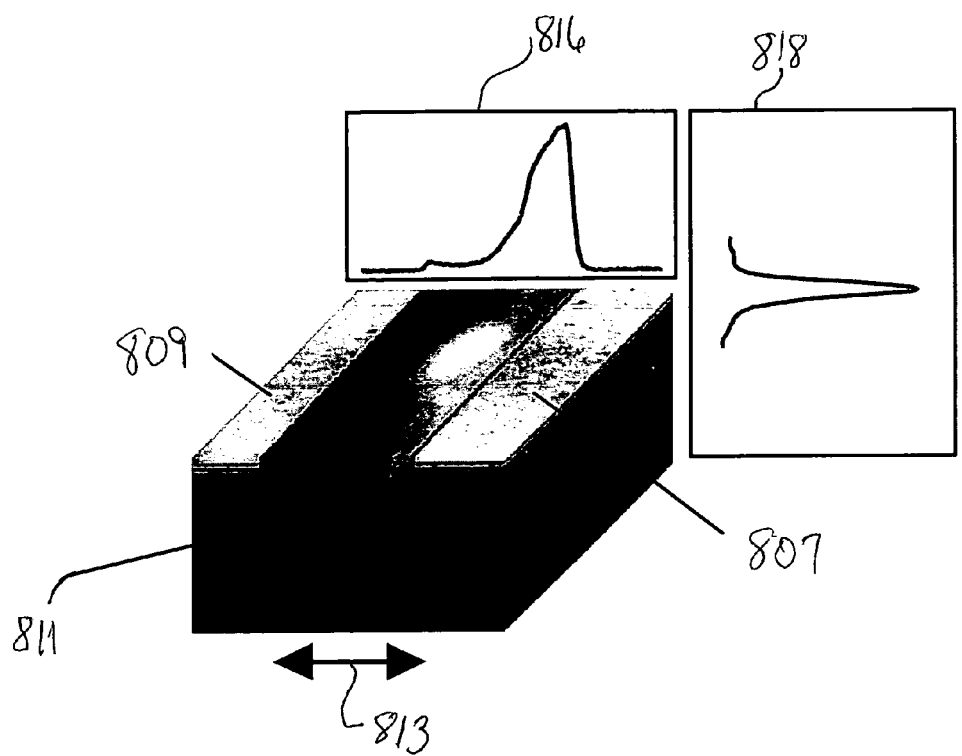
FIG. 8 shows an example of nonlinear scanning microscopy applied to 3D imaging of the two-photon current response in ZnSe.

FIG. 8 shows an example of nonlinear scanning microscopy applied to 3D imaging of the two-photon current response in ZnSe. Two-photon current image of a biased metal-ZnSe-metal structure is shown with a positive electrode 807 and a negative electrode 809 on opposite sides of a ZnSe body 811 with electrodes separated by distance 813 of 25 μm. Several two-dimensional scans taken at different depths are combined to produce a 3D image of the photocurrent. The graphs describe an average transverse response 816 and a longitudinal response 818. These images carry a wealth of information. For example, by comparing the response near the positive and negative electrode one can estimate the ratio of the electron to hole mobility. The depth response describes the effective crystal length from which a signal is obtained. This length is important for estimating the effect of dispersion on pulse autocorrelation measurements that use such two-photon current detectors as nonlinear elements. For a gap separation of a few microns, the temporal resolution of the ZnSe device has been estimated to be approximately 3 fs at λ=800 nm. This estimation includes the spectral response of the two-photon absorption (TPA).

Figure 9:
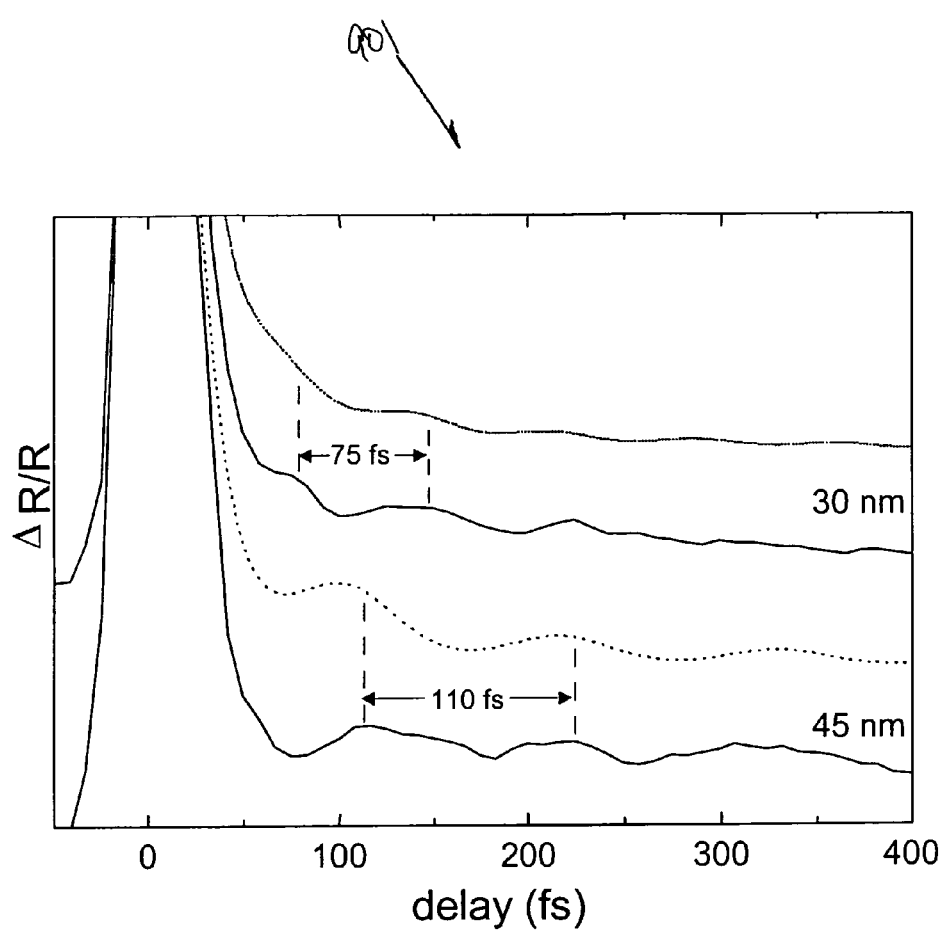
FIG. 9 shows periodic ballistic particle motion results in a modulation of the reflection signal of a fs pump-probe experiment utilizing surface plasmon resonance.

As is well known, nonlinear microscopy increases the resolution by a factor $n^{1/2}$ where n is the order of the nonlinearity. This is also true for material microstructuring. Direct writing two-photon photolithography has yielded the expected $\sqrt{2}$ increase in line density compared with common one-photon illumination. Recently, ballistic electron transport in thin gold films that resulted in a periodic bouncing of quasi-particles between the film boundaries has been observed. FIG. 9 shows periodic ballistic particle motion results 901 in a modulation of the reflection signal of a fs pump-probe experiment utilizing surface plasmon resonance. This was possible using plasmon mediated excitation and probing and the associated local field enhancement.

The area of biology/biophysics, such as cell membranes, is especially well suited to the technology of various embodiments of the present invention. On one hand, the processes of interest occur on length scales that challenge the resolution and imaging modes achievable with far-field light microscopy; on the other hand, membranes and membrane protein complexes are only a few nanometers thick, which enables the application of near-field techniques. It should also be noted that cell membranes play a central role in many aspects of cell biology, especially in cellular communication and signaling. For example, consider signaling in immune cells, and in particular in mast cells, which are central to the allergic response. Mast cells respond to foreign material (e.g. pollen grains or mimics) by activation and release of chemical mediators of inflammation. This signaling pathway, like many others, is initiated by the binding of the signaling agent (in this case, the allergen) to cell surface receptors, leading to their redistribution and/or reorientation in the cell membrane. The spatial relationships between receptors and auxiliary membrane proteins are thought to be critical to the biochemical mechanisms of signaling. In various embodiments, quantum dot and field enhancement arrays may be used to further our understanding of these spatial relationships.

Figure 10:
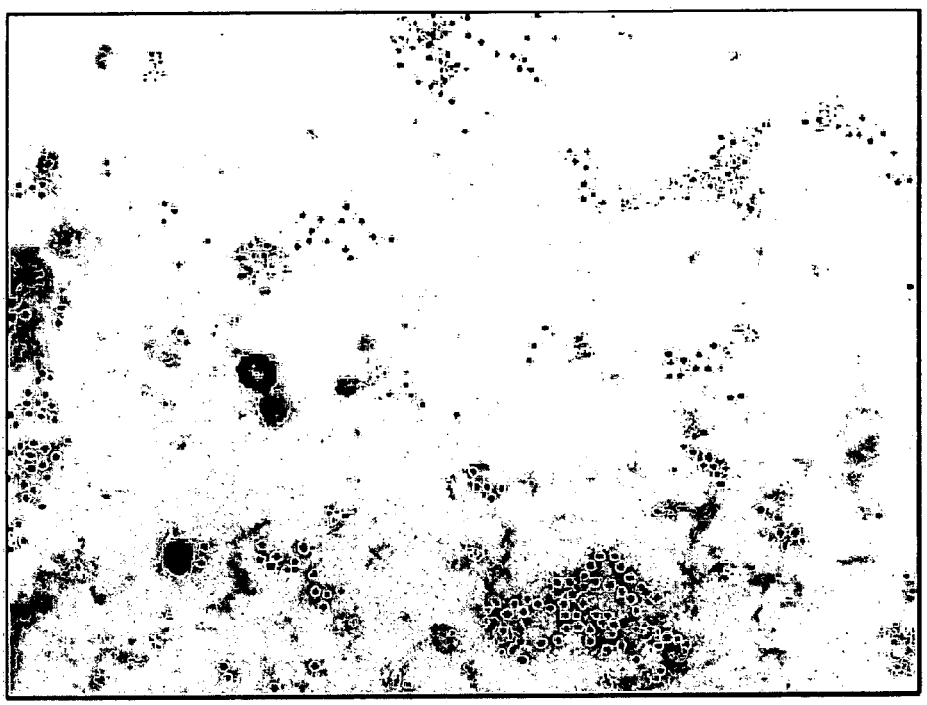
FIG. 10 shows an electron micrograph showing signaling proteins LAT (5 nm gold labels) and Thy-1 (10 nm) 10 minutes after Thy-1 crosslinking.

The flow of information through cells requires the constant remodeling of cell signaling and trafficking networks. To observe the remodeling events associated with receptor activation, researchers have generated and analyzed high resolution topographical maps of colloidal gold nanoprobes marking receptors and signaling proteins in native membranes by transmission electron microscopy (TEM). The technology involves labeling membrane sheets stripped from the dorsal cell surface with functionalized nanoprobes, imaging the labeled sheets by TEM, extracting probe coordinates from digitized images and analyzing the distributions of the probes with respect to each other and to membrane features like clathrin-coated pits and caveolae. The method for sheet preparation is based on a procedure originally described by researchers Sanan and Anderson (See, D. A. Sanan and R. G. W. Anderson, "Simultaneous Visualization of ldl Receptor Distribution and Clathrin Lattices on Membranes Torn from the Upper Surface of Cultured Cells," J. Histochem. Cytochem. 39 (1991) 1017-1024) and has been extensively described in the literature. It involves inverting cell monolayers (with and without manipulations including immunogold labeling from the outside) on glass coverslips onto poly-L-lysine-coated nickel EM grids. Pressure is applied briefly to the coverslip, upper cell surface adherent to the grid. After fixing in 2% paraformaldehyde, proteins are labeled from the inside by incubation with antibody-coated gold particles (2-10 nm). For electron microscopy, the samples are processed through glutaraldehyde, osmium, aqueous tannic acid and uranyl acetate, then air dried and images of technically acceptable membranes (no visible holes, folds or rips) are taken at 30-40,000×. The resulting images show an approximately 2.2×2.0 μm² area of the cell membrane that usually contains from a few hundred to a thousand gold probes. FIG. 10 shows an electron micrograph showing signaling proteins LAT (5 nm gold labels) and Thy-1 (10 nm) 10 minutes after Thy-1 crosslinking. See, Wilson, B., S. Steinberg, K. Liederman, J. Pfeiffer, Z. Surviladze, J. Zhang, L. Samelson, L-h Yang, P. Kotula, and J. M. Oliver. "Markers for Detergent-Resistant Lipid Rafts Occupy Distinct and Dynamic Domains in Native Membranes," Mol. Biol. Cell 15(6): 2580-2592. 2004. These proteins tend to colocalize more after crosslinking only the Thy-1. The images also reveal coated pits and other cell membrane features. Spatial point patterns of nanoprobe distributions have been extracted from digitized images and analyzed using several different statistics to define patterns of protein topographical segregation during signaling.

Results to date focus primarily on the IgE receptor-mediated signaling pathway of mast cells and basophils and the EGFR-mediated signaling pathways of ovarian and endometrial cancer cells. In both systems, receptors and signaling proteins are distributed non-randomly on the membranes of resting cells and receptor activation is associated with dynamic changes in protein topography. Statistical analyses reveal patterns of protein topographical segregation during signaling that are consistent with, although more complex than, the patterns of protein segregation into signaling pathways inferred from biochemical studies. Recent work addressed relationships between the signaling complexes defined by electron microscopy and the "lipid rafts" defined by others as detergent-resistant membrane fractions that are enriched in cholesterol, glycosphingolipids, and certain types of proteins (GPI-linked proteins, Src kinase family members) and have been proposed as sites for the assembly of signaling complexes. There is relatively little co-localization of the "raft markers" examined to date (including the Src kinase, Lyn, the GPI-linked protein, Thy-1, the cholera toxin-binding ganglioside, and the dually palmitoylated scaffolding proteins, LAT and NTAL) with either signaling complexes or with each other.

These results are broadly consistent with contemporary concepts about the mosaic organization of cell membranes. However, they also point to enormous gaps in our understanding of the size, composition and stability of lipid rafts and, in particular, of their roles in organizing signaling complexes at the membrane. Resolving this complexity will require alternative imaging techniques such as various embodiments of the present invention. Imaging of membrane sheets using near field optical microscopy may provide an entirely new impression of the organization of the cell membrane. Moreover, near-field harmonic microscopy will provide valuable information, in both cell sheets and on the basal (substrate-apposed) cell membrane of intact cells, on the disposition of membrane-associated proteins and on cell membrane potential, ultimately at length scales far below those limiting far-field techniques.

In various embodiments, QDs may be characterized with emission wavelength at approximately 1.3 µm and used for microscopic imaging. The characterization equipment may include mid-IR detectors and a Ti-sapphire laser/optical parametric oscillator.

For array-based microscopy, uniformity of the QDs is important. Quantum dot emission variability may be reduced to approximately 10 meV from current variability of 50 meV. To achieve this goal, the QD diameters should be ±1 nm. The QD size is directly related to the mask diameter of 200 nm±10 nm; several processing steps may be optimized to improve mask uniformity, including a minimized photolithographic exposure, thinned $SiO_2$ layer, and possibly a post-growth anneal process to catalyze In/Ga intermixing.

Even with great effort to promote uniformity, some variation may remain. Therefore, each array element (QD) may be characterized individually, with respect to emission rates, polarizations, and spectra. A fiducial marker on the array may be used to uniquely identify each QD source geometrically, in terms of its location from the origin or fiducial mark.

Quantum dot array characterization may include photoluminescence. To this end the array may be excited by a laser beam that is (x,y) raster-scanned across the structure while the luminescence $P_L$ is monitored with spectral resolution and for two orthogonal polarizations e. To first order, the response function $P_L(x,y,\lambda,e)$ can be used to correct luminescence images. The QD structures may be used applied to biological imaging. The QD arrays should be capped with a thin layer of, for example $SiO_2$, to avoid contamination by the specimen. The effect of this protective coating on $P_L(x,y,\lambda,e)$ can be determined. Increasing the QD emission towards the specimen made be provided by using reflection-enhancing layers below the substrate, as well as enhancing spontaneous emission of QDs by embedding in microcavities. The structure sizes of the QD arrays may allow study of single QDs, using local excitation and far-field photon detection, and by wide-field excitation and near-field microscopy.

To use fluorescence techniques, QDs with shorter wavelength luminescence are needed. Visible-red emission (650-750 nm) from quantum dots has been realized in the past few years, and these wavelengths are well suited to deep red and near-infrared fluorescent probes. There is increasing interest in the biomedical community in near-IR fluorescent probes, largely driven by the improved penetration depth and reduced scattering of IR light in tissue. In addition, biogenic autofluorescence is at a minimum in the near infrared. A variety of far-red and near-IR probes are commercially available, including the LI-COR IRDyes and the long-wavelength cyanine dyes, indocyanine green, and others. There has also been development of fluorescent metallic nanoparticles, such as gold nanoparticles grown on dendrimer scaffolds. These nanoparticles are water-soluble, are excitable at various wavelengths depending on size, and show good quantum yields compared to organic IR dyes. For example, 23-atom gold quantum dots were found to have an absorption maximum around 670 nm and a quantum yield of ~15%. There is growing availability of fluorescent labels in the far red/near-IR region. In an embodiment, quantum dots of differing composition, which can emit in the red and near-IR may be applied to various microscopy arrangements.

Visible-red emission from nanostructures has been achieved through the growth of InP quantum dots on InGaP latticed matched to GaAs, yielding emission wavelength in the 650-700 nm range and also by AlInAs quantum dots grown on AlGaAs, yielding emission wavelengths in the 700-750 nm range. The former has been demonstrated by both MBE and MOCVD, and has led to the development of red emitting QD lasers at room temperature. InP quantum dots on InGaP tend to exhibit a bimodal size distribution at lower growth temperatures, and more uniform distributions but lower dot densities at higher temperatures. This has been overcome to some degree by inserting a thin GaP layer, or by growing on InAlP lattice matched to GaAs. Variation in emission wavelength, band offset, and density of the dots can be achieved by varying the composition of the InGaP/InAlP off of the lattice match condition and by using InAlGaP layers on which to deposit InP when the design constraints of laser structure are not present. The InAlAs in AlGaAs system is relatively new and to date has only been tried by MBE. The InAlAs system thus far has been studied in the 700 nm plus emission regime. The ability to adjust the In/Al ratio, varying the band gap and strain, add flexibility to this material system in extending the wavelength range of visible emission. Additionally, there is the added practical benefit of not having to use a phosphorous-based material system.

Driving quantum dot arrays electrically may be used in order to achieve resolution below the current far-field limits. Toward this end quantum dot arrays may be constructed that are individually wired for addressable electroluminescence. Electroluminescence of single quantum dots has been reported in the literature. In most cases, a large number of dots were simultaneously excited. Researchers have also obtained light from a single dot by aperturing a diode that had a large number of InAs quantum dots at the pn junction. In an embodiment, a quantum dot array may be used to provide electroluminescence.

Figure 11:
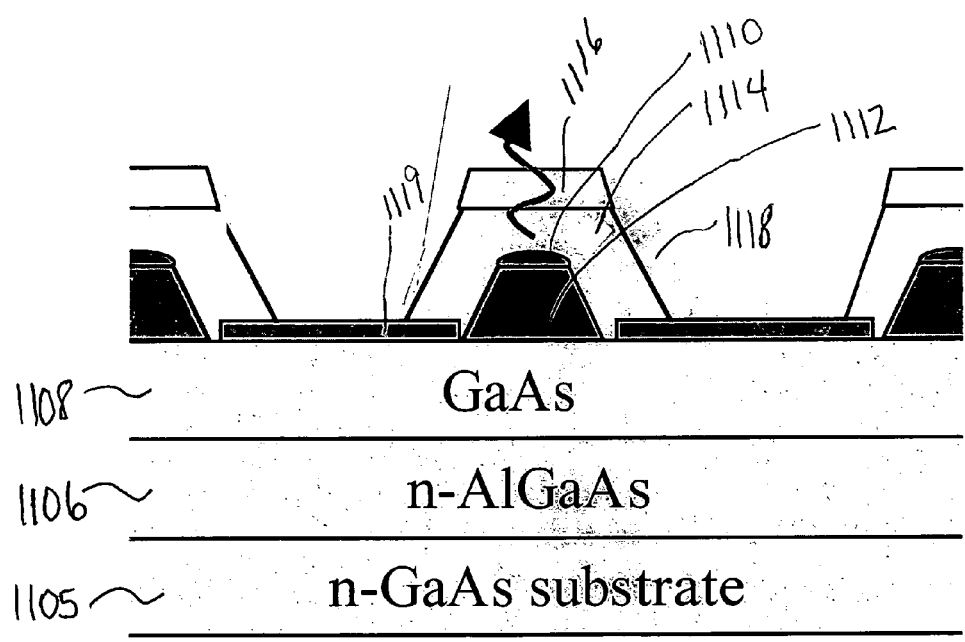
FIG. 11 illustrates an embodiment of an addressing configuration for electroluminescent quantum dot arrays.

FIG. 11 illustrates an embodiment of an addressable quantum dot 1110 with pyramid 1112 on a structure including a GaAs layer 1108 on an n-type GaAlAs layer 1106 on a n-type GaAs substrate. Embodiments for addressable QD arrays are not limited to GaAs-based materials, but may use other appropriate materials. Device structures may be designed to place patterned QDs less than 50 nm from the device surface in order to maximize resolution. This may be accomplished by capping the QDs with a thin undoped GaAs cap layer 1114 followed by a highly doped p-type GaAs ($p^+$-GaAs) contact layer 1116. The GaAs pyramid base widens crystallogaphically creating a broader base for metal deposition. A $SiO_2$ mask 1119 may be used between quantum dots. FIG. 11 shows that each QD to be individually electrically probed by depositing a thin line 1118 of gold on a wall of each pyramid making contact with the highly doped p-GaAs 1116. This scheme may be realized for a single line of QDs, where a single line of gold may be placed between the QDs. In an embodiment, individual electrical probing in a 2D array may be realized with the QD center to center spacing of approximately 500 nm to 1000 nm. Embodiments are not limited to these dimensions, but may have smaller or larger dimensions depending on the application. A processing scheme may be provided that allows both dense QD arrays as well as individual QD access.

In various embodiments, QD arrays may be used as sources to study supported lipid bilayers of several different compositions. To form an image, a stage holding the QD array with the contacting bilayer may be scanned, allowing the sequential excitation of each QD and the quantification of the emission. Though there are no fluorescence probes that can be excited by the existing mid-IR QD arrays, there are other methods to generate image contrast. For example, polarization effects at interfaces, such as used in Brewster angle microscopy to examine unlabeled supported lipid bilayers, may be used. QD arrays may be applied to explore whether the polarized QD emission can generate signals (i.e. whether the distribution of far-field radiation is altered) in the presence of cell membrane/water interfaces.

The long-wavelength QD arrays may also be used to study cell membrane sheets, using gold nanoparticles as labels. In various embodiments, application of QD arrays to microscopy may also reveal interesting protein dynamics. Scattering may fluctuate strongly as proteins move closer to and farther from a QD source. The protein dynamics can provide important information about protein oligomerization and cytoskeletal interactions.

The shorter-wavelength QD arrays may be used to image both supported lipid bilayers and cell membrane sheets containing labeled proteins and lipids. In an embodiment, QD excitation may be optical, using harmonics from a source such as a Ti-sapphire laser/optical parametric oscillator arrangement. In an embodiment, electroluminescent QD arrays may be used. In various embodiments, a QD spacing may have dimensions well below the far-field diffraction limit. Even widely spaced dot sources may permit new and important biophysical measurements. The QD sources may be used to excite the fluorescence of labeled proteins or lipids in a strongly distance-dependent manner, with non-radiative (Förster) energy transfer dominating at very small distances, and much weaker radiative/absorptive excitation at larger separations. Fluctuations in intensity (under single dot illumination) may provide information on molecular diffusion via fluorescence correlation spectroscopy over nanometer length scales.

Quantum dot arrays hold great promise for high resolution near field microscopy. Decreasing feature sizes in lithography will soon make is possible to position QDs much closer to each other than the visible or near-IR far-field resolution limit. However, these sources may never be useful for multiphoton excitation or harmonic microscopy, since quantum dots are inherently single photon emitters and thus cannot effectively excite multiphoton processes. For multiphoton applications, local field enhancement promises to provide near-field resolution capabilities.

In an embodiment, arrays of elements designed to provide strong local field enhancements, under illumination by red to mid-infrared light, may be used. Arrays of elements may vary from relatively simple structures to more complex structures that could be addressed through polarization and/or electrooptic effects. In various embodiments, array addressing may include methods that may extrapolate to length scales below the far-field resolution limit, permitting near-field resolution without mechanically scanning a tip.

Electronic plasma excitations at the surfaces of metals, or surface plasmons, result in strong absorption and scattering of light and give rise to a strongly enhanced electromagnetic field near the surface of the metal. The strong field enhancement has allowed for single-molecule surface enhanced Raman spectroscopy (SERS). There is also considerable interest in using plasmon field enhancement to increase fluorescence signals through surface-enhanced fluorescence, SEF. Unlike SERS, SEF signals decrease in very close proximity to the surface, owing to fluorescence quenching via energy transfer to the metal. The quenching effect is strong only at very short distances (typically <<10 nm), while field enhancement effects extend outward to much larger distances. Thus, fluorescence can be readily observed in protein monolayers and lipid bilayers on metals and has been used to image 100 nm lipid vesicles adsorbed onto a gold metal surface. The field enhancement effects have been particularly useful for multiphoton excitation and harmonic microscopies, where high local field intensities are essential to obtaining good signals.

Much work has been done studying the field enhancement effects of nanoparticles and islands. Metallic nanoparticles have been called "nanoantennas" for near field optical microscopy, because of their ability to direct electromagnetic radiation at a resonant frequency into strong local field enhancements, through the localized surface plasmon effect. Local field enhancements can be calculated by a variety of computational methods, including the discrete dipole approximation, finite difference time domain methods, multiple multipole method, and the modified long wavelength approximation. In general, both the size and the shape of the nanoparticle impact the plasmon resonance and the field enhancement properties. Highly elongated nanoparticles have at least two plasmon resonance frequencies, one corresponding to electron oscillation along the long axis, and a higher frequency resonance corresponding to transverse electronic excitation. These orthogonal excitations couple into orthogonal polarizations of the incident illumination.

The basic principle of field enhancement introduced above can be understood by considering the classic problem of a sphere of radius $R<<\lambda$ and dielectric constant $\epsilon_1$ embedded in a material with dielectric constant $\epsilon_2$. In the presence of an external electric field $E_0$ parallel to the z-axis, the field near the sphere can be written as $$E_{out}(x, y, z) = E_0 \vec{e}_z - \alpha E_0 \left[ \frac{\vec{e}_z}{r^5} - \frac{3z}{r^5}(z\vec{e}_z + y\vec{e}_y + x\vec{e}_x) \right], \quad (1)$$

where $$r^2 = x^2 + y^2 + z^2 \text{ and } \alpha = R^3 \left[ \frac{\epsilon_1 - \epsilon_2}{\epsilon_1 + 2\epsilon_2} \right]$$

is the polarizability.

Although this is an electrostatic model, it often allows one to discuss the main qualitative features of field enhancement that can be expected from illumination with electromagnetic waves. At certain frequencies the denominator in Eq. (1) can become small for a metal sphere in a dielectric environment [$Re(\epsilon_1)<0$ and $Re(\epsilon_2)>0$], and the field enhancement peaks at this resonance. It is also important to note that this resonance depends both on the material of the nanostructure (and shape) and the dielectric constant of the surrounding medium. At the surface of the sphere the field enhancement is maximal (minimal) in the direction of (perpendicular to) the external field with a field ratio of 2. Much larger field-enhancement ratios occur for non-spherical objects for two orthogonal polarizations. The field enhancement and its location may be illustrated schematically for an array of squares.

In nonlinear microscopy a field enhancement q will produce an overall signal enhancement of $q^{2n}$, where n is the order of the nonlinearity. For example, n=2, 3 for two-photon fluorescence and third-harmonic generation, respectively.

Suppose there are m imaging channels, that is, m independent ways to address and trigger imaging of a regular array of pixels. The inter-pixel length of each of the m arrays, d, is matched to the optical (far-field) resolution of the microscope. If these m arrays are regularly interlaced the effective pixel distance after m images are combined becomes $d2^{(1-m)/2}$. For structures like the squares shown in FIG. 12, excitation by two orthogonal polarizations, m=2, may result in a resolution increase of approximately 1.4.

Less research has been focused on organized arrays of metallic nanostructures than on isolated nanoparticles. An additional complication here is that the separate elements may interact; a calculation for an isolated nanostructure will not necessarily be appropriate to describe a closely spaced array of structures. For example, in plasmon-assisted transmission of IR light though an array of annuli, the spacing between the annuli is critical in the response of the array, bringing the non-local surface plasmon excitation into resonance with the response of each annulus. Roughly speaking, the array features should be dominated by the properties of the individual structures only if the elements are separated by more than the average spatial extent of the outward field enhancement, and if they are surrounded by an insulating material that does not support electronic resonances of its own.

Figure 12:
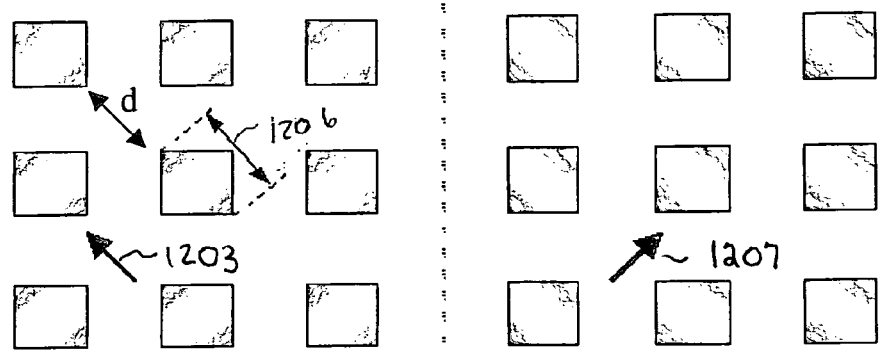
FIG. 12 illustrates an embodiment of field enhancement produced by an array of squares.

FIG. 12 illustrates an embodiment of field enhancement produced by an array of squares. Such structures may include square arrays of square metal (gold or silver) islands. The arrows 1203, 1207 show the direction of the external field, which may be the polarization direction of a laser.

Figure 13:
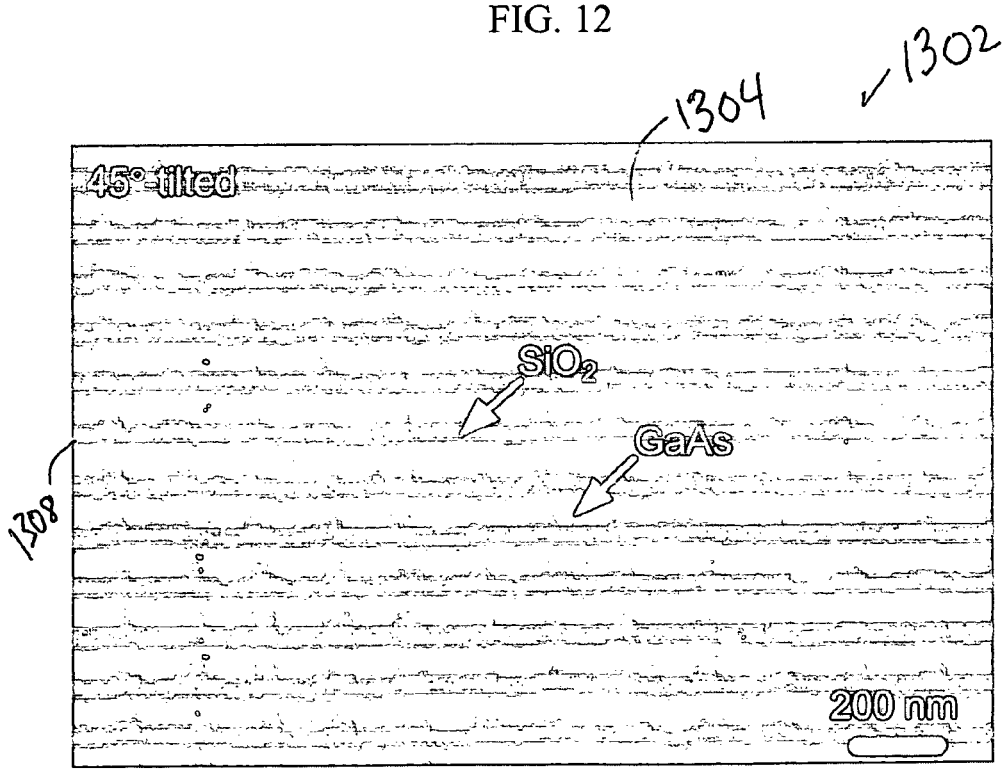
FIG. 13 illustrates a 180 nm pitch square array on GaAs, fabricated using interference lithography.

FIG. 13 illustrates a 180 nm pitch square array 1302 on GaAs 1304, fabricated using interference lithography. Parallel lines 1308 of $SiO_2$ are formed in square array 1303. Such techniques may be used to make square metal arrays. The work demonstrated in FIG. 13 has been conducted by colleagues in the S. R. J. Brueck research group of the Center for High Technology Materials (CHTM) at the University of New Mexico.

Structures may include square arrays of square metal (gold or silver) islands, see FIGS. 12 and 13. The metal islands may have approximately 100 nm edge length; the separation, d, between the islands may be varied, with a minimum center to center separation of about 200-300 nm. Calculations of the electromagnetic fields around triangular 60 nm silver particles from other researchers, for example, has shown a >40-fold electric field enhancement for regions within about 20 nm of a vertex, and >10-fold enhancement out to about 40 nm. The intensity enhancements are the squares of these values, i.e. 100-fold to >1600-fold, and the enhancement in a two-photon fluorescence excitation or second harmonic generation would be $10^4$ to greater than $10^6$ (ignoring metal quenching effects on fluorescence). In previous studies described in the literature, the silver islands showed a strong in-plane dipole resonance when excited by CW 700 nm light; other, much weaker quadrupole resonances were observed at substantially shorter wavelengths. The desired nonlinear signal generation requires the excitation with ultrashort, femtosecond light pulses.

Square structures will certainly show dipolar plasmon resonances as well, with strong field enhancements at the corners. The two (m=2) independent images can be taken with excitation at two orthogonal polarizations 1203, 1207 along the diagonals 1206 of the square. Thus, even a simple array structure may provide improved lateral resolution in microscopy applications. As explained above, by using two orthogonal polarizations, the number of pixels in the image can be doubled. The resolution enhancement with this method may be limited to polarization-independent microscopies. However, in many biological applications, fast molecular motion averages out polarization effects.

In various embodiments, arrayed structures may provide for quantitatively understanding the dependence of field enhancement on the wavelength, polarization, and pulse duration of the exciting laser, both theoretically and experimentally. Theoretical predictions may be made using the discrete dipole approximation or other calculational tools. For modeling, the electrostatic approach may be modified and include electrodynamic corrections such as radiation damping and dynamic depolarization. In an embodiment, structures may be addressed successively, providing sufficiently large field enhancements at excitation wavelengths suitable for biological specimens such that the structures may be technologically feasible to produce.

Measurements of the dynamic response may be made using a source such as a 10-fs Ti:sapphire laser and frequency tunable optical parametric oscillator. Ultrashort light pulses allow for rapid excitation of the electrons in the material; the relaxation through electron-electron and electron-phonon coupling can then be studied by pump-probe spectroscopy. The probe pulse, with an adjustable time delay from approximately 10 fs to hundreds of picoseconds, then probes some optical property of the material, such as the transient absorption, transmission, or reflectivity. The technique has been extensively applied by researchers to suspensions of nanoparticles and to gold films excited at the surface plasmon resonance. The likely result of such experiments is an estimate for the electron-electron, electron-phonon and electron-defect scattering times. These quantities can then be used in the modeling of the field enhancement.

Measurements of field enhancement may be made by depositing (spin coating) a thin polymer film containing fluorescent dye onto the substrate. On excitation of the metal island surface plasmons, the fluorescence may be detected with either a CCD camera or an avalanche photodiode in a mirror-scanning microscope. Fluorophores that require a two- and a three-photon excitation may be used, as multiphoton processes will naturally be more responsive to field enhancement.

One of the potential problems is fluorescence quenching, which manifests itself as a decrease in fluorescence efficiency and fluorescent lifetime. Therefore, in addition to the fluorescence intensity images, the lifetime across the structure may be mapped. In an experiment, the pulsed excitation laser across may be scanned across the array and the lifetime may be measured with an available time-correlated single-photon counter. By measuring both the lifetime and the intensity, the field enhancement effect and the quenching effect may be separable. IR-excitable dyes, as well as two-photon visible dyes may be used.

For the structures developed with spacings smaller than the resolution of far-field techniques, these measurements may be performed with optical near-field techniques using near-field scanning optical microscopy (NSOM). There are two principal operational modes: (i) local excitation with a fiber tip and global collection of luminescence, and (ii) global excitation and local collection of the luminescence. The suitability of (i) and (ii) may be tested with respect to maximum signal generation and minimum affect of the tip on the luminescence behavior.

Measurements of the spatial range of the field enhancement effects can be made using Langmuir-Blodgett techniques to deposit multilayer membranes onto the field enhancement substrates. Such techniques have been used to examine the range of quenching by metal surfaces. Alternatively, spacer layers may be deposited between the metal structures and the dye-doped film.

Field enhancement islands offer unique opportunities for sub-wavelength optical measurements. Consider a small metallic island that is much smaller than the optical resolution limit. A dipolar plasmon excitation along the diagonal will excite fluorophores (or harmonic generation) from sample molecules in the vicinity of the opposite corners. Regardless of the size of the island, it will be possible to determine the contribution from each corner separately. Because the dimension of the island is known, the far-field asymmetry in the (diffraction-smeared) image can be used to "deconvolute" the signal. In essence, the island structure converts the resolution problem into a precision issue. Analogously, the positions of proteins labeled with nanoscopic gold particles can be determined to a precision of better than a nanometer. These small islands don't increase image "resolution", but they could function very well to track protein diffusive movements in their vicinity. In addition, smaller islands may be necessary in order to adjust the plasmon resonance frequency to particular desired optical frequencies.

Figure 14:
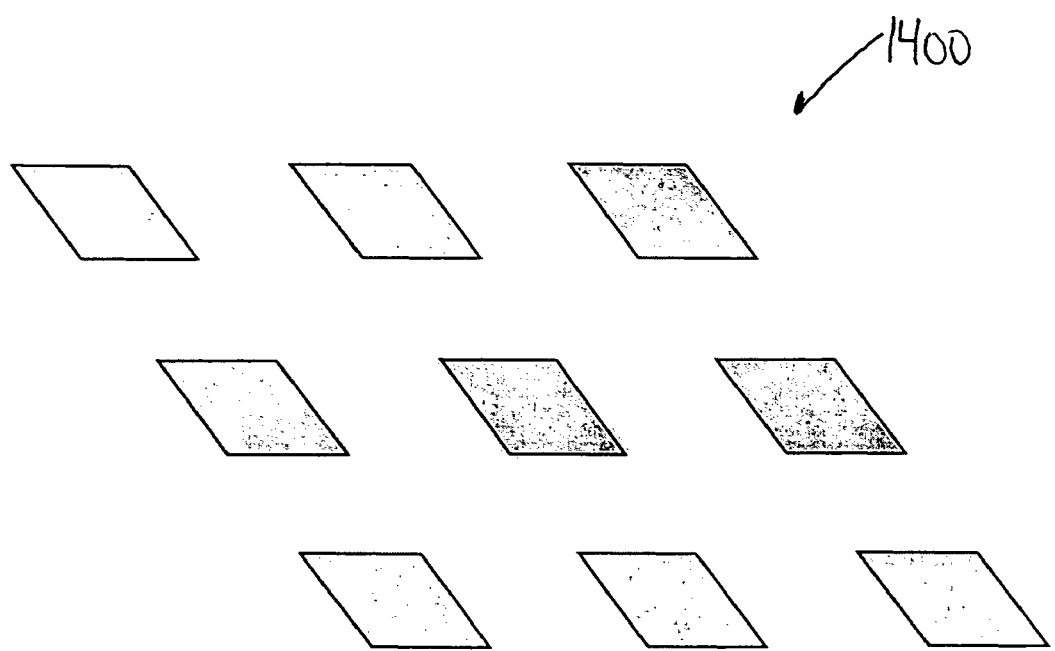
FIG. 14 shows an embodiment of an array of metallic diamonds.

In various embodiments, arrays may be constructed with differing island sizes and separations, including more complex island shapes, such as parallelogram 'diamonds'. FIG. 14 shows an embodiment of an array 1400 of metallic diamonds. Metallic diamonds will exhibit distinct plasmon resonances along their long and short dimensions. In an embodiment, island sizes may be 50-100 nm, and separations may be approximately 200 nm. Embodiments are not limited to these dimensions, but may have smaller or larger dimensions depending on the application. Field enhancement strengths, resonance frequencies, and polarizations will be different at the distinct corners. With anisotropic structures, it is expected that the plasmon resonances parallel and perpendicular to the long axis will be excited by different polarizations, as well as different wavelengths of light, as has been observed with highly anisotropic nanocrystals.

Field enhancement techniques are very powerful for all areas of non-linear spectroscopy, including Raman spectroscopy, coherent anti-Stokes Raman spectroscopy (CARS), multiphoton fluorescence, and harmonic generation. In various embodiments, field enhancement techniques may be directed to second harmonic generation (SHG) at cell membranes, on both intact cells and supported lipid bilayers. Second harmonic generation is especially powerful for studying membranes and membrane-associated molecules. The locally anisotropic environment at charged surfaces gives rise to SHG signals from water; membrane potential affects the alignment of the water dipoles and thus directly (though weakly) affects SHG signals allowing the measurement of membrane potential without introducing dyes into the membrane. Molecules containing chromophores can give quite strong resonant second harmonic signals when oriented at cell or lipid bilayer membranes. It should be possible to generate signals from unlabeled proteins by harmonic resonance with tryptophan or tyrosine residues at 280 nm; tryptophan has been studied by second harmonic generation at the air-water interface.

In various embodiments, two key biological issues relating to the stimulation of RBL cells with antigen may be studied with field enhanced SHG: 1) the recruitment of signaling proteins (especially the Syk kinase) to the plasma membrane, and 2) the modulation of cell membrane potential after stimulation with antigen. Although Syk is a cytosolic protein, it is known to be recruited to phosphorylated IgE receptors as part of the cellular activation process. The spatial and temporal features of recruitment are critical to the underlying activation biochemistry; high-spatial resolution SHG can provide novel insight into this important problem. In an embodiment, to study this recruitment, the array surfaces may be allowed to adsorb a model antigen, dinitrophenol-serum albumin (DNP-BSA), and RBL cells (previously "primed" by the binding of anti-DNP-IgE to IgE receptors) may be allowed to "plate" onto this activating surface during experimentation. Control experiments, in which DNP-BSA is added to cells already adherent, may indicate whether membrane recruitment is localized to regions of receptor cross-linking.

RBL cells have been known to undergo antigen-mediated membrane depolarization since the early 1980s and have even been used as model systems for comparative studies of membrane potential-sensitive fluorescent dyes. The membrane potential plays an important role in intracellular spatial and temporal calcium oscillations. These oscillations in turn are thought to enhance the efficacy of the intracellular calcium signal in causing secretion. A better understanding of the spatial and temporal dynamics of membrane potential changes is thus critical to fully understanding the RBL secretory mechanism.

In an embodiment, field enhancement may be used with cell membrane sheets and supported lipid bilayers and liposomes. Experiments on these simpler, more accessible systems may allow one to properly interpret whole cell experiments. Although liposomes tend to rupture when brought in contact with surfaces, a surface treatment that attenuates the van der Waal's attraction and allows stable adhesion of intact liposomes may be used. Stably adherent liposomes may then be used for membrane potential studies, using ionophores, and for protein adsorption studies.

In an embodiment, a general approach includes making SHG imaging measurements, using field enhancement, both with and without exogenous dyes/labels. The imaging may be accomplished with a CCD camera and with focused and polarized laser excitation of surface plasmons in nanoscale island arrays. High resolution spatial information on membrane potential and Syk kinase membrane interactions may greatly improve our understanding of signaling in RBL cells.

The full promise of a plasmon field enhancement near-field array for microscopy may be realized when each element can be individually addressed in some manner. It is important to note that it is not essential that one element be turned 'on' while all others are 'off'; it would be sufficient to be able to modulate the field at a specified element; then, lock-in detection or simple subtractive imaging could be used to isolate signals resulting from excitation by that particular element. Embodiments include at least two different general addressing strategies.

Surface plasmon resonances depend critically on the optical properties of the surrounding local environment (cf. Eqn 1 above). This is the operational principle behind the commercial Biacore surface plasmon sensors, widely used to measure protein and DNA binding interactions. Changes in electrical potential can affect the local environment, and small shifts in plasmon resonance angle have been seen with planar gold films in aqueous solutions. Studies have shown that localized surface plasmon resonances in metal islands are shifted by varying the thicknesses of a 15-36 nm overcoating of $SiO_2$; the changes were attributed to changes in the nanoparticles' dielectric environment.

Figure 15:
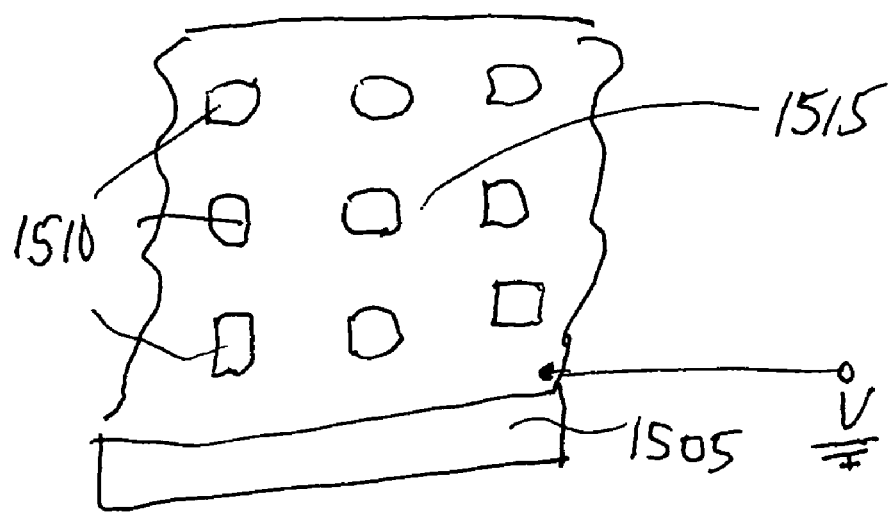
FIG. 15 illustrates a representation of an embodiment of islands surrounded by electrooptic material on a substrate.

FIG. 15 illustrates a representation of an embodiment of islands 1510 surrounded by electrooptic material 1515 on a substrate 1505. Islands may be regions of conductive material. In an embodiment, an electrooptically active material, such as lithium niobate or PLZT, may be deposited in the region between metal islands. On applying large DC fields to this material, the index of refraction can be changed. Preliminary experiments may be performed using electric fields applied to large regions of the sample to determine whether electrooptic effects can be seen and to ascertain their magnitude. The fields may be applied with electrodes to demonstrate the principle and measure the effect on plasmon resonances. In an embodiment, small contacts may be used in an integrated fashion.

Figure 16:
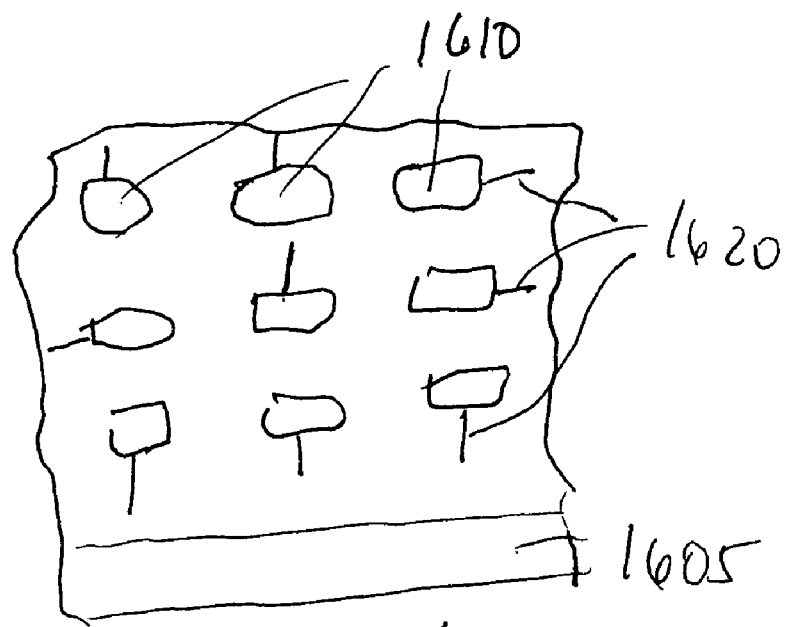
FIG. 16 illustrates a representation of an embodiment of an array of islands with each island coupled to a wire.
Figure 17:
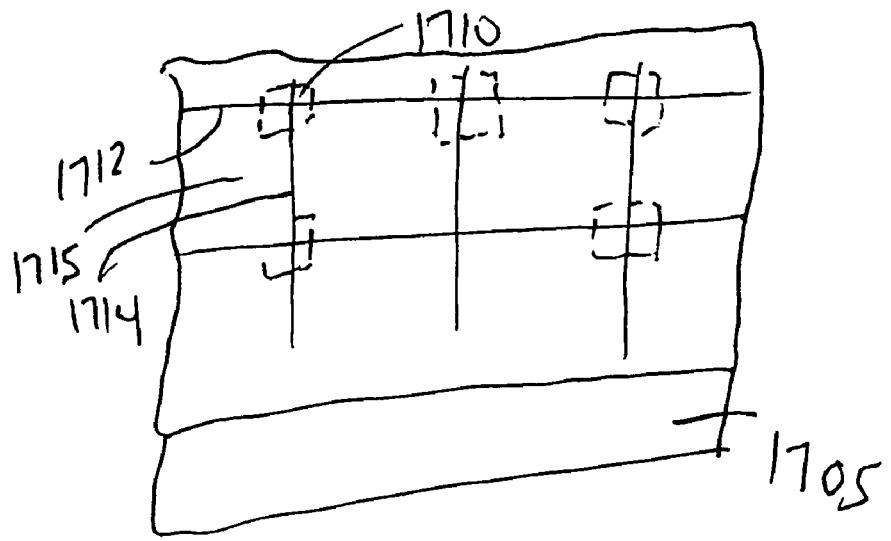
FIG. 17 illustrates a representation of an embodiment of a linear array of wires on a substrate constructed with in two orthogonal grids separated by electrooptic material.

FIG. 16 illustrates a representation of an embodiment of an array of islands 1610 on a substrate 1605 with each island coupled to a wire 1620. (Partial wiring 1620 is shown with connections to sources not shown). Local electric fields may be applied by wiring 1620 to each island in an array (requiring $n^2$ wires for an n×n array). Alternatively, a separate wiring system designed to allow local field application may be used. FIG. 17 illustrates a representation of an embodiment of a linear array of wires on a substrate 1705 constructed with in two orthogonal grids 1712, 1714 separated by electrooptic material 1715. Applying a voltage difference between selected horizontal and vertical conductors will create a large field localized to the crossing point, thereby addressing the intersection where an island 1710 may be vertically located to be affected by the large localized field.

In an embodiment, a mechanism for modulating surface plasmon field enhancement may include a structure to control conduction electron density. In a field-effect transistor, for example, conductivity is modulated by an electric-field induced increase in carrier density. There is clear evidence that plasmon effects can be modulated in field effect transistors in the terahertz frequency regime. The absorption of terahertz radiation in a double quantum well field effect transistor was examined in the literature. It is not yet clear whether such structures can be designed to take advantage of this effect to obtain large electric fields external to the device. Appropriately designed nanoscale transistors may be used to explore whether such effects can be observed in near-IR. If this approach proves feasible, it may open up a very attractive addressing modality for array-based field-enhancement microscopy.

In an embodiment, thermal methods may include using $VO_2$, which has a semiconductor-to-metal thermal transition at 67° C. Above the transition temperature, nanorods formed from this material (in an $SiO_2$ matrix) can readily support localized surface plasmon excitations. Absorbance at $\lambda>1.0$ µm as been shown to increase accordingly.

Figure 18:
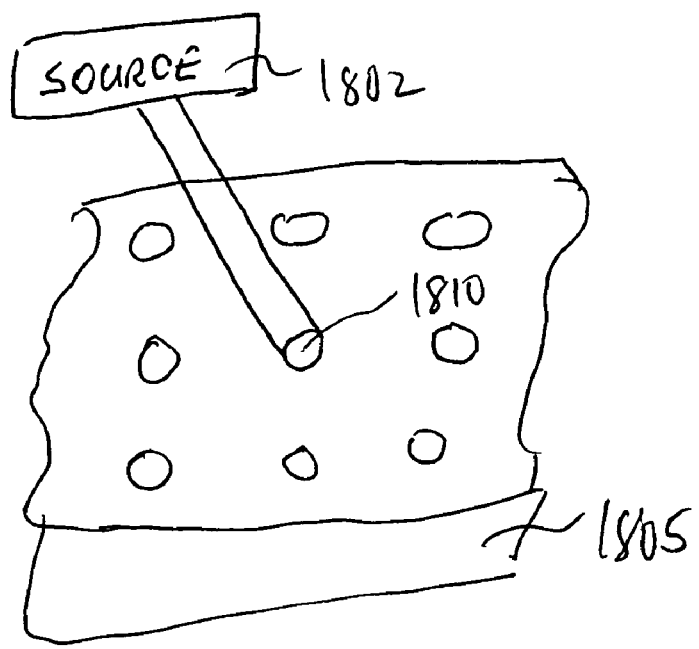
FIG. 18 depicts a representation of an embodiment of an arrangement in which a source illuminates an island in an array of islands on a substrate, where the material of each island undergoes a semiconductor-metal transition at a temperature characteristic of the material.

FIG. 18 depicts an embodiment of an arrangement in which a source 1802 illuminates an island 1810 in an array of islands on a substrate 1805, where the material of each island undergoes a semiconductor-metal transitions at a temperature characteristic of the material. In an embodiment, localized heating with femtosecond pulses may drive $VO_2$ nanoparticles through the semiconductor-to-metal transition, initiating localized surface plasmon resonances. Short pulses with fluences of a few $mJ/cm^2$ have been shown to raise the temperature of gold nanoparticles to the melting point, resulting in shape conversion from rods to spheres. Much lower powers may be used for $VO_2$, warming it to just above its semiconductor-to-metal transition temperature. Because heat dissipation occurs rapidly and in all three dimensions from a hot nanoparticle, the resulting temperature increase at the sample could be quite negligible. Most importantly, the inherent non-linearity of this process could be used to selectively activate a nanoparticle at the center of the laser focus, while particles a short distance off-center (but still much closer than the optical resolution limit) remain non-conductive.

In an embodiment, QD arrays may be characterized, and used to study gold nanoparticle-labeled membrane proteins. The short-range diffusion of these proteins may be measured by correlation spectroscopy. Possible QD polarization-based imaging methods for membranes may be used. Plasmon enhancement of two-photon fluorescence of red and near-IR dyes in model films may be measured. Near field optical microscopy may be used to map the fluorescence source distribution. Time-resolved measurements may yield information on the transients of the field enhancement and electron dynamics.

Visible QD arrays may be used to excite red or near IR fluorescent dyes in cells and membrane sheets. Fluorescence correlation spectroscopy may be used with these point sources. Modeling studies may lead to the design and construction of new metal island arrays, excitable in the red or near IR. The arrays may be used to study two-photon fluorescence and SHG in membranes and cells. SHG may be used to measure the membrane association of Syk protein, using exogenous labeling for resonant SHG.

In various embodiments, electrical addressing of QD arrays may be used. Such addressing may eventually allow QD arrays to function well below the far-field resolution limit. Electrooptic (EO) materials may be incorporated into metal island arrays and the electrooptic shift of the plasmon response may be quantified. Metal arrays of alternative shapes (e.g. diamonds) may be created and used for SHG experiments. Plasmon resonances in nanotransistors may be studied and used as an alternative route to addressing. SHG measurements of unlabeled biological systems may be conducted using various embodiments of the present invention. Control experiments on membranes and liposomes may measure SHG from (unlabeled) protein adsorption, and from membrane potentials.

Figure 19:
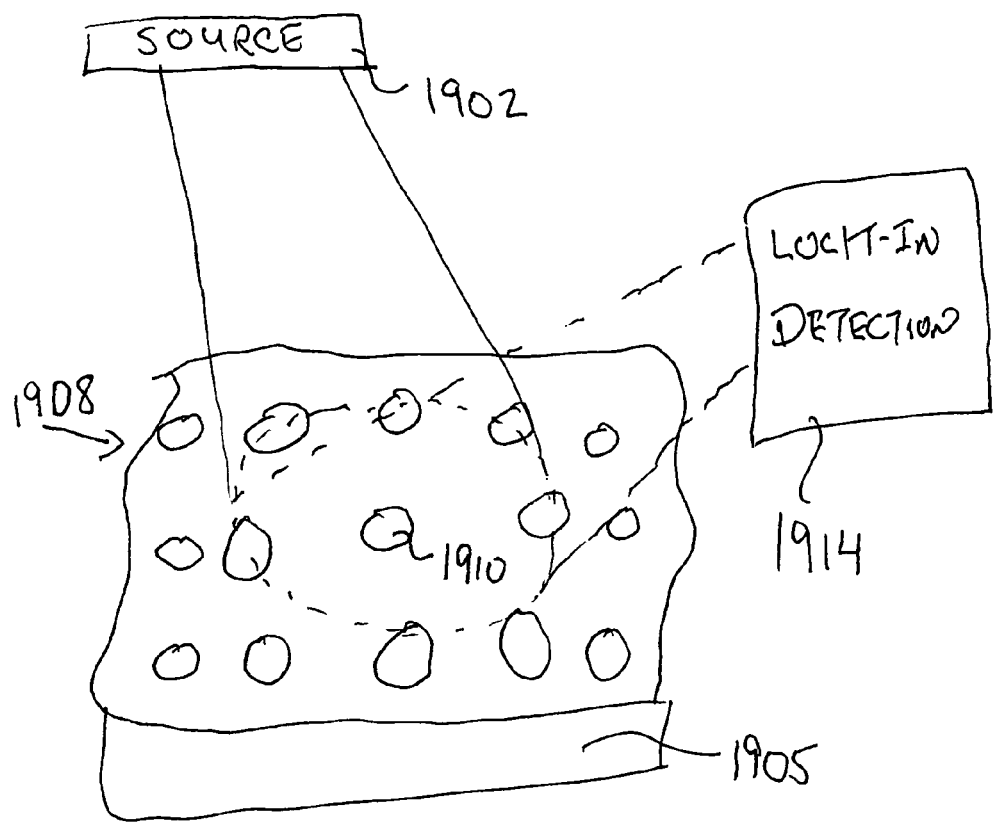
FIG. 19 depicts a representation of an embodiment of a source illuminating a nanostructured array on a substrate in which a signal from a single element is obtained by lock-in detection.

FIG. 19 depicts a source 1902 illuminating a nanostrutured array 1908 on a substrate 1905 in which a signal from a single element 1910 is obtained by lock-in detection 1914. QD arrays with spacings below the far-field resolution limit may allow unprecedented resolution in studies of membrane protein distribution in signaling cells. Local fields may be achieved with plasmon/EO arrays, allowing lock-in techniques to pull out the plasmon-enhanced signal from a single element. With obtainment of nanotransistor plasmon resonances, field enhancement may be applied in these structures. Quantum dots and field enhancement arrays, along with novel island shapes and QD arrays with reflective underlayers, may be applied to biophysical studies.

In various embodiments, microscopy with sub-resolution nanometer-scale arrays ("nanoscopy") may be usefully applied to understanding signal transduction pathways in RBL cells.

The concept of stimulated emission for superresolution fluorescence microscopy has been developed by Hell and co-workers. See, S. W. Hell and J. Wichmann, "Breaking the Diffraction Resolution Limit by Stimulated Emission: Stimulated-Emission-Depletion Fluorescence Microscopy," Opt. Lett. 19 (1994) 780-782.

The mechanism for superresolution is described here with respect to FIG. 20 in which two lasers are used. As noted above, this mechanism described with respect to FIG. 20 finds its origins in the work of Stefan W. Hell on far-field stimulated emission for supperresolution microscopy. The first laser beam, propagating in the usual $TEM_{00}$ (Gaussian) mode at the excitation wavelength of the target fluorescent molecule (fluor), is focused to a diffraction-limited spot in the sample. It excites fluors within that spot. A second laser, propagating in a "doughnut" shaped mode, at the emission wavelength of the fluor, is focused to a doughnut that surrounds and partially overlaps the spot of the first laser. This laser causes stimulated emission of fluors in the doughnut ring, which add their fluorescence to the second laser beam. Only fluors near the very center of the doughnut ring escape stimulated emission, and can emit fluorescence isotropically. Fluorescence is detected in the backward (or upstream) direction. The doughnut mode (a superposition of $TEM_{01}$ and $TEM_{10}$ modes) can stimulate emission anywhere that the intensity is non-zero. By increasing the intensity of the doughnut beam, the original excited fluor spatial distribution is "trimmed" more and more at its edges, leaving only a very small region of fluors at the center that can emit isotropic fluorescence.

Figures 20A, 20B, 20C:
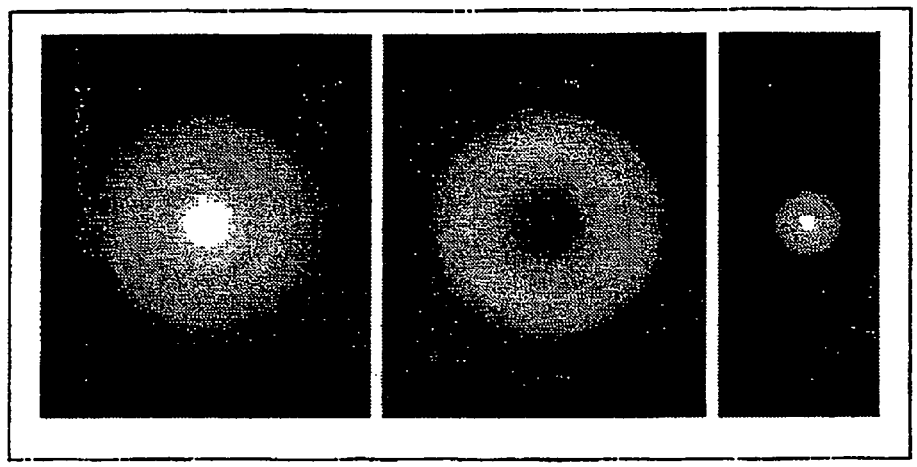
FIGS. 20A-20D illustrate stimulated emission for superresolution microscopy.
Figure 20D:
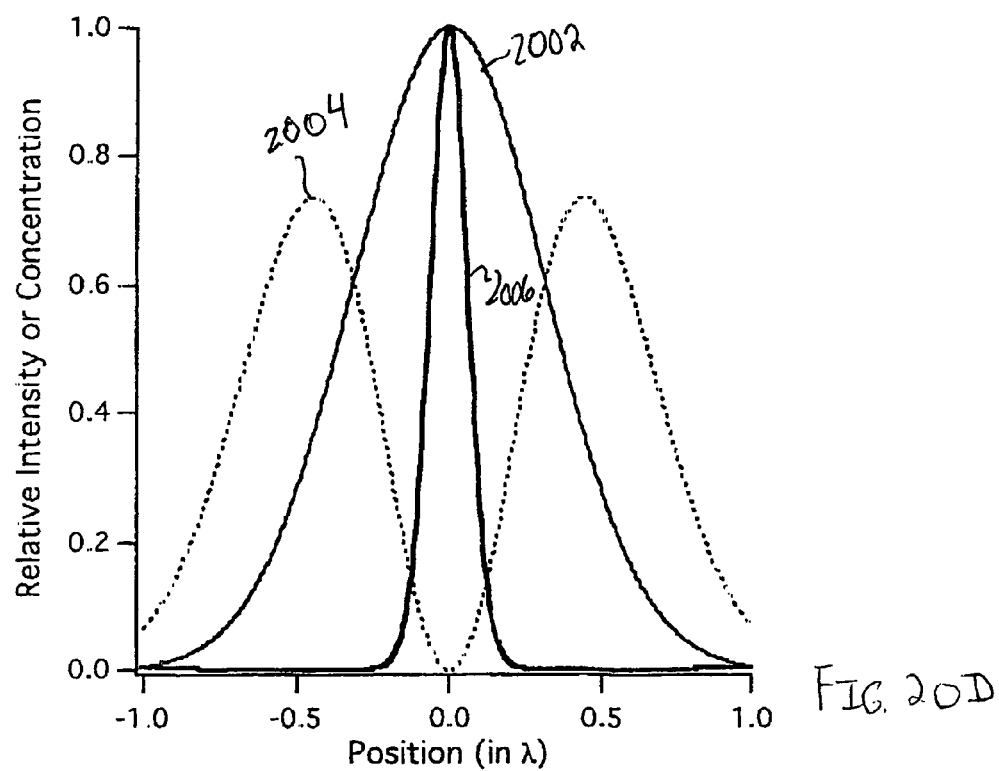

FIGS. 20A-20D show stimulated emission for superresolution microscopy. In FIG. 20A, a Gaussian beam excites fluorophores in a diffraction-limited spot. In FIG. 20B, a doughnut beam causes stimulated emission, thus "trimming" the spot of excited fluors. Only fluors in the center of the spot, the small center spot of FIG. 20C, do not experience stimulated emission; these then decay isotropically and are detected. The process is illustrated in the graph of FIG. 20D. Curve 2002 represents the excitation beam. Curve 2004 represents the doughnut beam for stimulated emission. Curve 2006 represents the remaining fluors after stimulated emission.

Hell's work is a breakthrough in superresolution microscopy, but has the significant disadvantage of requiring very precise beam alignment. Thus, the technique cannot be used with beam scanning microscopy.

Surface plasmons are electronic excitations and associated electromagnetic fields that can be produced at the surfaces of metallic films and particles by interaction with light. These electromagnetic fields are also capable of causing stimulated emission.

In an embodiment, a method for fluorescence microscopy achieves superresolution by stimulated emission into plasmon fields. The plasmon fields may be created in a patterned metal-island substrate, which may be produced by electron beam lithography. Once the patterned metal-island substrate is made, the locations of the plasmon fields are fixed and do not require alignment. This may allow for more rapid imaging through scanning techniques. Typically, in such a technique, the sample should reside close to the substrate.

A discussion of such a method follows. For clarity, imaging in one dimension is presented. Consider first a single metal island. A plasmon excitation in this island will cause stimulated emission of fluors that are nearby. "Nearby" is determined by the strength of the plasmon excitation, since the field weakens rapidly with increasing distance from the metal island. A strong plasmon excitation will cause significant stimulated emission out to a considerable distance ($\sim\lambda$) from the island, while a weak plasmon excitation will only stimulate emission from very close fluors. The effect is illustrated in FIG. 21.

Figure 21:
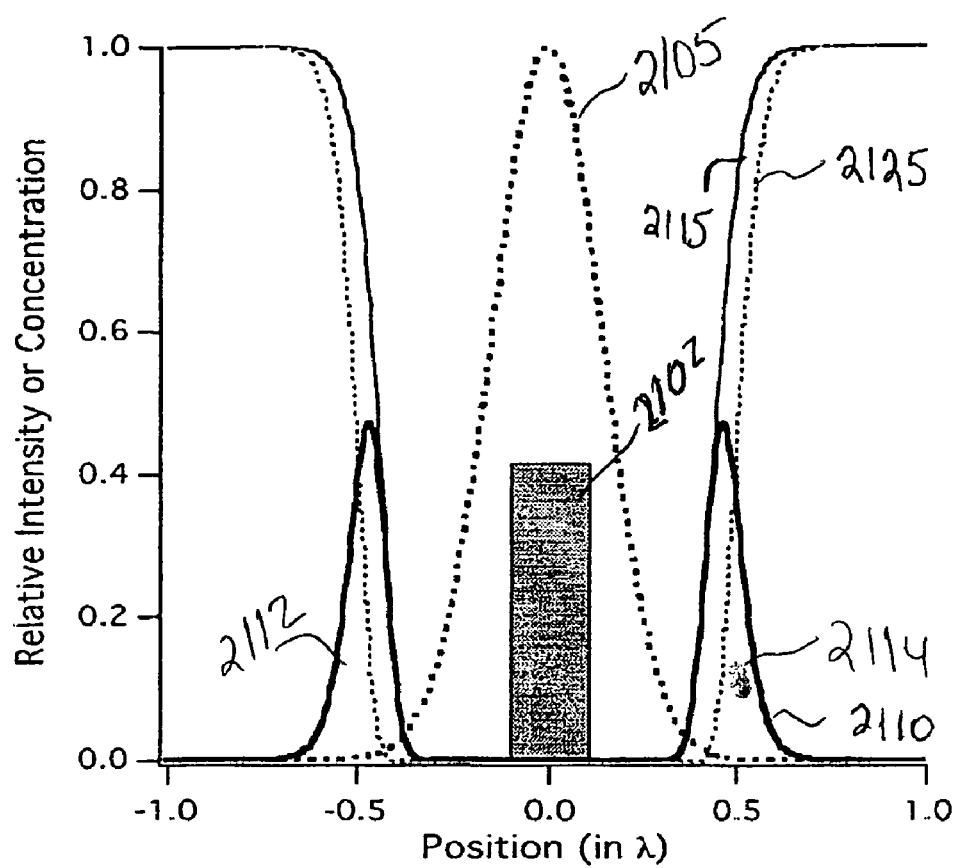
FIG. 21 depicts an embodiment of a metal nanoisland that gives rise to a plasmon field, when excited by laser light.

FIG. 21 depicts an embodiment of a metal nanoisland 2102 (symbolically shown by the box) that gives rise to a plasmon field, shown in curve 2105, when excited by laser light. This plasmon field will cause stimulated emission of fluorophores that are close to the metal island. The remaining fluors will fluoresce; their distribution is shown by curve 2115. If the plasmon field is made stronger (by increasing the intensity of the exciting laser), the stimulated emission will depopulate excited fluors to a greater distance, shown by curve 2125. The difference between the two images is caused by the fluors that are "at the boundary", shown by curve 2110. Most importantly, the width of the difference distributions are significantly smaller than the width of the plasmon field itself, and significantly smaller than the diffraction-limited width of a focused beam.

In an embodiment of the present invention, the fact that the range of stimulated emission depends on the plasmon intensity is used to obtain superresolution imaging. The subtraction of two images, one taken at high plasmon intensity from one taken at lower plasmon intensity, may be employed. Only those fluors that are located in the boundary regions 2112, 2114 in FIG. 21 will be imaged. These regions have a width that is far smaller than the far-field optical resolution limit. In fact, the lower limit on the region size may be set only by signal strength requirements, not by any wavelength-dependent phenomenon.

Of course, as shown in FIG. 21, there are two regions 2112, 2114 (in the one dimensional example) that would be imaged by the subtraction technique. These regions may be differentiated by their response to plasmons on the other islands nearby. Region 2112 will experience some stimulated emission from an island on the left, while region 2114 will show much less. The nearby islands would be separated by the far-field resolution, so that they can be independently excited.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments, will be apparent to those of skill in the art upon studying the above description. The scope of the invention includes any other applications in which the above structures and fabrication methods are used.

What is claimed is:

1. A method comprising:
   illuminating a nanoscale array of islands with an electromagnetic signal;
   addressing the nanoscale array to differentiate signals from different islands of the nanoscale array, the differentiated signals originating from illuminating the nanoscale array; and
   applying the differentiated signals to microscopy of a specimen.

2. The method of claim 1, wherein the method includes:
   generating a plasmon field at an island using a laser to provide a first image, the plasmon field having an intensity;
   increasing the intensity of the plasmon field to provide a second image; and
   subtracting the two images.

3. The method of claim 2, wherein the method includes using responses to plasmons on other islands in the nanoscale array to differentiate regions generated from subtracting the two images.

4. The method of claim 1, wherein applying the differentiated signals to microscopy of a specimen includes applying enhanced electromagnetic fields.

5. The method of claim 1, wherein applying the differentiated signals to microscopy of a specimen includes applying fluorescence emission.

6. The method of claim 1, wherein addressing the nanoscale array includes modulating an electromagnetic field enhancement effect at a selected island and using lock-in detection to isolate a signal originating from the selected island.

7. The method of claim 1, wherein addressing the nanoscale array includes applying a local electric field to electrooptic material surrounding a selected island.

8. The method of claim 1, wherein addressing the nanoscale array includes centering a laser beam over a selected island to cause a semiconductor-to-metal transition of the selected island.

9. The method of claim 1, wherein addressing the nanoscale array includes applying two orthogonal polarizations of exciting light to a selected island to provide field enhancement at two sets of opposite corners of the selected island, the islands being square metallic islands.

10. The method of claim 1, wherein addressing the nanoscale array includes applying electromagnetic signal as exciting light to the nanoscale array of islands, the nanoscale array of islands being an interlaced grid of islands with each island having a shape responsive to a specific excitation beam profile.

11. The method of claim 1, wherein illuminating a nanoscale array of islands includes illuminating a nanoscale array of metallic islands.

12. The method of claim 1, wherein illuminating a nanoscale array of islands includes illuminating a nanoscale array of semiconductor islands.

13. The method of claim 1, wherein illuminating a nanoscale array of islands includes illuminating an array of quantum dots.

14. The method of claim 1, wherein illuminating a nanoscale array of islands includes illuminating an array of field enhancement elements.

15. The method of claim 1, wherein the method includes microscopy of a biological specimen.

16. The method of claim 1, wherein the method includes microscopy of a synthetic bilayer membrane.

17. The method of claim 1, wherein the method includes microscopy of a lipid bilayer.

18. The method of claim 1, wherein the method includes microscopy of protein dynamics.

19. The method of claim 1, wherein the method includes applying field enhanced second harmonic generation to analyze recruitment of signaling proteins to a plasma membrane.

20. The method of claim 1, wherein the method includes applying field enhanced second harmonic generation to analyze modulation of cell membrane potential after stimulation with antigen.

21. An apparatus comprising:
a nanoscale array of islands;
a means to direct electromagnetic radiation to the nanoscale array of islands;
a means to address an island in the nanoscale array; and
a means to apply electromagnetic signals originating from the addressed island after incidence of the electromagnetic radiation on the addressed island to provide microscopy of a specimen.

22. The apparatus of claim 21, wherein the means to direct electromagnetic radiation to the nanoscale array of islands includes a laser.

23. The apparatus of claim 21, wherein the means to address an island in the nanoscale array of islands includes electrooptic material adjacent the island.

24. The apparatus of claim 21, wherein the means to address an island in the nanoscale array of islands includes a laser configured to center a beam of light onto the island, the island having material that undergoes a semiconductor-metal transition in a temperature range.

25. The apparatus of claim 21, wherein the means to address an island in the nanoscale array of islands includes a plurality of polarizable sources of electromagnetic radiation to illuminate the island, the island having a shape to generate an enhanced field on illumination by the plurality of polarizable sources.

26. The apparatus of claim 21, wherein the means to apply electromagnetic signals originating from the addressed island after incident of the electromagnetic radiation on the addressed island to microscopy of a specimen includes a structure to place the specimen in proximity to the nanoscale array of islands.

27. An apparatus comprising:
a nanoscale array of islands;
a source of electromagnetic radiation to illuminate an island in the nanoscale array to provide an enhanced electromagnetic field; and
a holder to configure the nanoscale array and a specimen in a relative position to provide interaction of the enhanced electromagnetic field with the specimen.

28. The apparatus of claim 27, wherein the nanoscale array of islands includes an addressable nanoscale array of islands.

29. The apparatus of claim 27, wherein the nanoscale array of islands includes a nanoscale array of metallic islands.

30. The apparatus of claim 27, wherein the nanoscale array of islands includes a nanoscale array of semiconductor islands.

31. The apparatus of claim 27, wherein the nanoscale array of islands includes an array of quantum dots.

32. The apparatus of claim 31, wherein the array of quantum dots includes an array of InAs quantum dots.

33. The apparatus of claim 27, wherein the nanoscale array of islands includes
a n-type GaAs substrate;
a layer of n-type AlGaAs on the n-type GaAs substrate;
a layer of GaAs on the layer of n-type AlGaAs;
a pyramid structure on the layer of GaAs;
a quantum dot on the pyramid structure;
an undoped GaAs cap layer on the quantum dot;
a layer of highly doped p-type GaAs on the undoped GaAs cap layer; and
a line of conductive material on a wall of the pyramid structure making contact with the layer of highly doped p-GaAs.

34. The apparatus of claim 33, wherein the line of conductive material includes gold.

35. The apparatus of claim 27, wherein the nanoscale array of islands includes a nanoscale array of field enhancement elements.

36. The apparatus of claim 27, wherein the apparatus includes electrooptic material surrounding each island in the nanoscale array.

37. The apparatus of claim 27, wherein each island includes material having a semiconductor-metal transition property and the apparatus includes a laser source configured to center a beam over a selected island to cause semiconductor-metal transition in the selected island.

38. The apparatus of claim 27, wherein each island includes square metallic material and the apparatus includes sources to provide two orthogonal polarizations of exciting light to a selected island to provide field enhancement at two sets of opposite corners of the selected island.

39. The apparatus of claim 27, wherein the nanoscale array of islands is configured as an interlaced grid of islands with each island having a shape responsive to a specific excitation beam profile.

40. The apparatus of claim 27, wherein the holder includes a substrate on which the nanoscale array is disposed.

41. A method comprising:
providing a nanoscale array of islands;
providing a source of electromagnetic radiation to illuminate an island in the nanoscale array to provide an enhanced electromagnetic field; and
providing a holder to configure the nanoscale array and a specimen in a relative position to provide interaction of the enhanced electromagnetic field with the specimen.

42. The method of claim 41, wherein providing a nanoscale array of islands includes providing a nanoscale array of islands formed using interferometric lithography.

43. The method of claim 41, wherein providing a nanoscale array of islands includes providing a nanoscale array of metal islands formed using electron beam lithography.

44. The method of claim 41, wherein providing nanoscale array of islands includes providing the nanoscale array of islands with each island formed by:
   forming a layer of n-type AlGaAs on a n-type GaAs substrate;
   forming a layer of GaAs on the layer of n-type AlGaAs;
   forming a pyramid structure on the layer of GaAs;
   forming a quantum dot on the pyramid structure;
   forming an undoped GaAs cap layer on the quantum dot;
   forming a layer of highly doped p-type GaAs on the undoped GaAs cap layer; and
   depositing a line of conductive material on a wall of the pyramid structure making contact with the layer of highly doped p-GaAs.

45. The method of claim 44, wherein depositing a line of conductive material includes depositing a line of gold.

46. The method of claim 44, wherein forming a quantum dot includes placing the quantum dot less than 50 nm from the layer of GaAs on which the pyramid is disposed.

47. The method of claim 41, wherein providing a source of electromagnetic radiation to illuminate an island in the nanoscale array includes providing a scanning source of electromagnetic radiation.

48. The method of claim 41, wherein providing a holder includes providing the nanoscale array on a substrate.

* * * * *